United States Patent
Swaminathan et al.

(10) Patent No.: US 6,410,702 B1
(45) Date of Patent: Jun. 25, 2002

(54) MODIFIED INTERNUCLEOSIDE LINKAGES (II)

(75) Inventors: Sundaramoorthi Swaminathan; Mark Matteucci; Jeff Pudlo, all of Burlingame; Robert J. Jones, Daly City, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/165,883

(22) Filed: Oct. 2, 1998

Related U.S. Application Data

(62) Division of application No. 07/892,902, filed on Jun. 1, 1992, now Pat. No. 5,817,781.

(51) Int. Cl.[7] .................. C07H 21/02; C07H 21/04; C07H 19/00; C12Q 1/68; A01N 43/04
(52) U.S. Cl. .................. 536/23.1; 536/22.1; 536/25.2; 536/25.3; 514/43; 514/44; 435/6
(58) Field of Search .............................. 536/22.1, 25.2, 536/25.3, 23.1; 514/43, 44; 435/6

(56) References Cited

U.S. PATENT DOCUMENTS

| | | | |
|---|---|---|---|
| 4,959,463 A | 9/1990 | Froehler et al. | 536/27 |
| 5,034,506 A | 7/1991 | Summerton et al. | 528/391 |
| 5,079,151 A | 1/1992 | Lampson et al. | 436/91 |
| 5,138,045 A | 8/1992 | Cook et al. | 536/27 |
| 5,223,618 A | 6/1993 | Cook et al. | 544/276 |
| 5,264,564 A | 11/1993 | Matteucci | 536/23.1 |
| 5,272,057 A | 12/1993 | Smulson et al. | 435/6 |
| 5,378,825 A * | 1/1995 | Cook et al. | 536/25.34 |
| 5,399,676 A | 3/1995 | Froehler | 536/23.1 |
| 5,470,967 A * | 11/1995 | Huie et al. | 536/24.3 |
| 5,489,677 A * | 2/1996 | Sanghvi et al. | 536/22.1 |
| 5,527,899 A | 6/1996 | Froehler | 536/25.3 |
| 5,596,086 A | 1/1997 | Matteucci et al. | 536/22.1 |
| 5,817,781 A * | 10/1998 | Swaminathan et al. | 536/22.1 |
| 5,969,118 A * | 10/1999 | Sanghvi et al. | 536/22.1 |

FOREIGN PATENT DOCUMENTS

| | | |
|---|---|---|
| WO | WO 86/05518 | 9/1986 |
| WO | WO 89/12060 | 12/1989 |
| WO | WO 91/06626 | 5/1991 |
| WO | WO 91/14436 | 10/1991 |
| WO | WO 91/15500 | 10/1991 |
| WO | WO 92/02534 | 2/1992 |
| WO | WO 92/05186 | 4/1992 |

OTHER PUBLICATIONS

Agrawal, S. et al., "Oligodeoxynucleoside phosphoramidates and phosphorothioates as inhibitors of human immunodeficiency virus", *Proc. Natl. Acad Sci.*, 1988, 85, 7079–7083.

(List continued on next page.)

*Primary Examiner*—Jezia Riley
(74) *Attorney, Agent, or Firm*—Woodcock Washburn LLP

(57) ABSTRACT

The invention relates to novel modified oligonucleotides, the construction thereof, and their use in oligonucleotide-based therapies. More specifically, the invention is to novel oligonucleotides having modified internucleoside linkages which are resistant to nucleases, having enhanced ability to penetrate cells, and which are capable of binding target oligonucleotide sequences in vitro and in vivo. The modified oligonucleotides of the invention are particularly useful in oligonucleotide-based therapies utilizing the modified oligonucleotides to interrupt protein synthesis or transcription or to otherwise inactivate messenger RNA or double stranded DNA.

5 Claims, 18 Drawing Sheets

OTHER PUBLICATIONS

Agrawal et al., *Nucl. Acids. Res.*, 1979, 6, 3009–3024.

Asseline, U. et al., "Nucleic acid–binding molecules with high affinity and base sequence specificity: Intercalating agents covalently linked to oligodeoxynucleotides", *Proc. Natl. Acad. Sci.*, 1984, 81, 3297–3301.

Beal, P. A. et al., "Second Structural Motif for Recognition of DNA by Oligonucleotide–Directed Triple–Helix Formation," *Science*, 1991, 251, 1360–1363.

Clontech, "Advertisement," *Nucl. Acids Res.*, 1991, 19(23).

Cocuzza, "A Phosphoramidite Reagent for Automated Solid Phase Syntehsis of 5'–Biotinylated Oligonucleotides," *Tetra. Lett.*, 1989, 46, 6287–6290.

Costick et al., "Solid Phase Synthesis of Oligonucleotides Containing 3'–Thiothymidine," *Tetra. Lett.*, 1989, 30, 4693–4696.

Coull, J.M. et al., "Synthesis and Characterization of a Carbamate–Linked Oligonucleoside", *Tetrahedron Letts.*, 1987, 28, 745–748.

Froehler, B.C. et al., "Oligodeoxynucleotides Containing C–5 Propyne Analogs of 2'–Deoxyuridine and 2'–Deoxycytidine", *Tetrahedron Letts.*, 1992, 33, 5307–5310.

Horne et al., "Recognition of Mixed–Sequence Duplex DNA by Alternate–Strand Triple–Helix Formation," *J. Am. Chem. Soc.*, 1990, 112, 2435–2437.

Inoue et al., *Nucl. Acids Res.*, 1985, 13(19), 7119–7128.

Kierzek, R. et. al., "Association of 2'–5'Oligoribonucleotides" *Nucl. Acids Res.*, 1992, 20, 1685–1690.

Letsinger, R.L. et al., "Cationic Oligonucleotides", *J. Am. Chem. Soc.*, 1988, 110, 4470–4471.

Matteucci, M., "Deoxyoligonucleotide Analogs Based on Formacetal Linkages", *Tetrahedron Letts.*, 1990, 31, 2385–2388.

Peninsula Laboratories, "Advertisement," *Nucl. Acids Res.*, 1991, 19(22).

Petrie et al., "A Novel Biotinylated Adenylate Analogue Derived from Pyrazolo[3,4–d]pyrimidine for Labeling DNA Probes," *Bioconjugate Chem.*, 1991, 2, 441–446.

Pudlo et al., "Deoxyoligonucleotides Containing 2', 5' Acetal Linkages: Synthesis and Hybridization Properties," *Tetra. Lett.*, 1994, 35(50), 9315–9318.

Stawinski et al., "Studies on the t–butyldimethylsilyl group as 2'–O–protection in oligoribonucleotide synthesis via the H–phosphonate approach," *Nucl. Acids Res.*, 1988, 16, 9285–9298.

Stein, C.A. et al., "Oligodeoxynucleotides as Inhibitors of Gene Expression: A Review", *Cancer Res.*, 1988, 48, 2659–2668.

Stirchak, E.P. et al., "Uncharged Stereoregular Nucleic Acid Analogs. I. Synthesis of a Cytosine–Containing Oligomer with Carbamate Internucleoside Linkages", *J. Org Chem.*, 1987, 52, 4202–4206.

Uhlmann, E. et al., "Antisense Oligonucleotides: A New Therapeutic Principle", *Chem. Reviews*, 1990, 90, 544–584.

Young, S. L. et al., "Triple Helix Formation Inhibits Transcription Elongation In Vitro," *Proc. Natl. Acad. Sci.* USA, 1991, 88, 10023–10026.

\* cited by examiner

Figure 1, Reaction Scheme 1

Figure 2, Reaction Scheme 2

Figure 3, Reaction Scheme 3

Figure 5, Reaction Scheme 5

Figure 6, Reaction Scheme 6

Figure 7, Reaction Scheme 7

Figure 8, Reaction Scheme 8

Figure 9, Reaction Scheme 9

Figure 10, Reaction Scheme 10

Figure 11, Reaction Scheme 11

Figure 12, Reaction Scheme 12

Figure 13, Reaction Scheme 13

Figure 14, Reaction Scheme 14

Figure 15, Reaction Scheme 15

Figure 16, Reaction Scheme 16

Figure 17, Reaction Scheme 17

Figure 18/19, Reaction Scheme 18/19
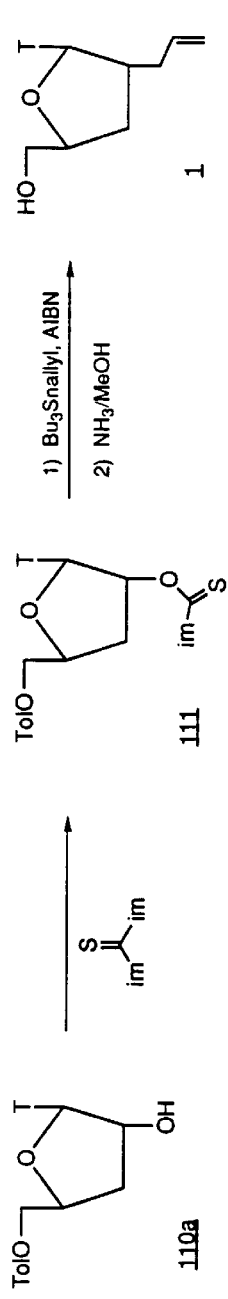
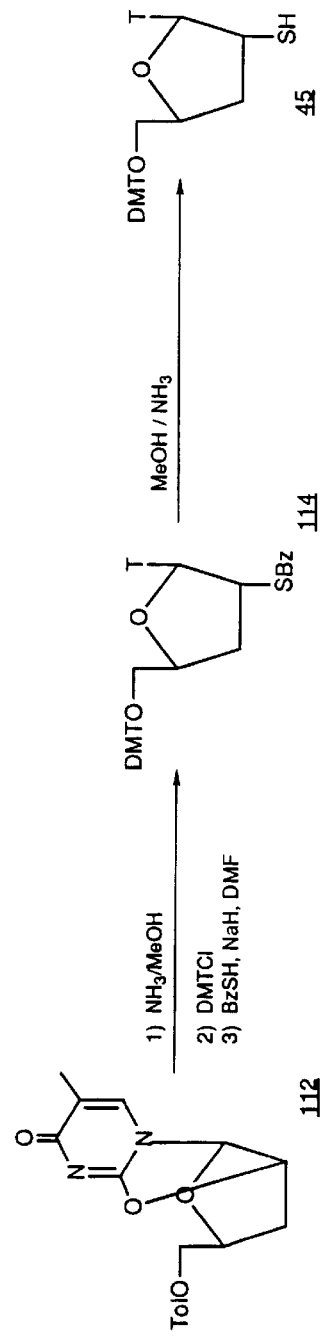
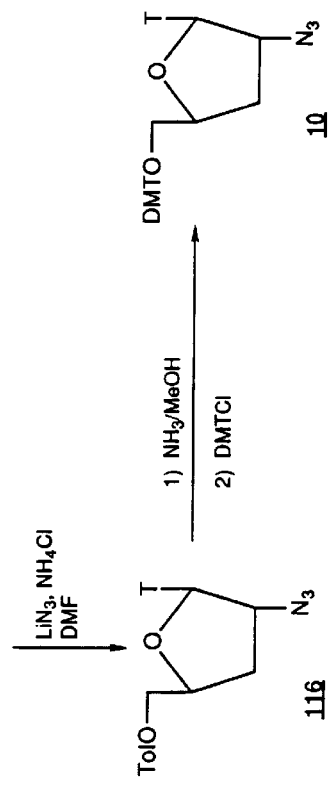
Figure 18
Figure 19

MODIFIED INTERNUCLEOSIDE LINKAGES (II)

This application is a divisional of patent application Ser. No. 07/892,902, filed Jun. 1, 1992, now U.S. Pat. No. 5,817,781, and claims priority from international application Ser. No. PCT/US91/06855, filed Sep. 20, 1991.

FIELD OF THE INVENTION

The invention relates to novel modified oligonucleotides, the construction thereof, and their use in oligonucleotide-based therapies. More specifically, the invention is to novel oligonucleotides having modified internucleoside linkages which are resistant to nucleases, having enhanced ability to penetrate cells, and which are capable of binding target oligonucleotide sequences in vitro and in vivo. The modified oligonucleotides of the invention are particularly useful in oligonucleotide-based therapies utilizing the modified oligonucleotides to interrupt protein synthesis or otherwise inactivate messenger RNA or double stranded DNA.

BACKGROUND OF THE INVENTION

The application of oligonucleotides and oligonucleotide analogs (oligomers) for therapeutic uses represents a relatively new development in drug design and discovery. Several fundamental therapeutic approaches that utilize oligomers have been proposed.

One approach is based largely on interfering with gene expression through oligomer binding to a complementary RNA sequence. This application is known as "antisense" therapy because the oligomer base sequence is identical to the antisense strand of the gene that gave rise to the RNA (Uhlmann, E., et al., *Chem Reviews* (1990) 90:543–584;and Stein, C. A., et al., *Cancer Res* (1988) 48:2659–2668). Another approach, referred to herein as "triple helix" therapy utilizes oligomers that bind to duplex DNA as detailed below. Binding to a target DNA is sequence specific but involves different base pairing binding. Both antisense and triple helix therapies exert therapeutic effects via binding to nucleic acid sequences that are responsible for disease conditions. Such sequences are found in the genome of pathogenic organisms including bacteria, protozoa, yeasts, parasites, fungi or viruses or may be endogenous sequences (oncogenes). By modulating the expression of a gene important for establishment, maintenance or elimination of a disease condition, the corresponding condition may be cured, prevented or ameliorated.

Another therapeutic approach that is based on the use of oligomers includes generation of "aptamers" and is disclosed and claimed in commonly owned application Ser. Nos. 745,215, 659,980 and 658,849.This approach utilizes oligomers that specifically bind to proteins thereby interfering with their function. The use of oligomers that mimic the structure of certain RNA molecules that are bound by intracellular proteins has also been adduced as a therapeutic approach as described in international application no. PCT/US91/01822.

Antisense oligonucleotides are synthetic oligonucleotides which bind complementary nucleic acids (i.e. sense strand sequences) via hydrogen bonding, thereby inhibiting translation of these sequences. Therapeutic intervention at the nucleic acid level using antisense oligonucleotides offers a number of advantages. For example, gene expression can be inhibited using antisense or triple helix oligomers. Inhibition of gene expression is more efficient than inhibition of the protein encoded by the gene since transcription of a single DNA sequence gives rise to multiple copies of mRNA which, in turn, are translated into many protein molecules.

Antisense and triple helix therapies for diseases whose etiology is characterized by, or associated with, specific DNA or RNA sequences, are particularly useful. The oligomer employed as the therapeutic agent can be directly administered or generated in situ and is one that is complementary to a DNA or RNA needed for the progress of the disease. The oligomer specifically binds to this target nucleic acid sequence, thus disturbing its ordinary function.

An oligomer having a base sequence complementary to that of an mRNA which encodes a protein necessary for the progress of the disease, is particularly useful. By hybridizing specifically to this mRNA, the synthesis of the protein will be interrupted. However, it is also possible to bind double-stranded DNA using an appropriate oligomer capable of effecting the formation of a specific triple helix by inserting the administered oligomer into the major groove of the double-helical DNA. The resulting triple helix structure can then interfere with transcription of the target gene (Young, S. L. et al., *Proc Natl Acad Sci* (1991) 88:10023–10026).

An important feature of therapeutic oligomers is the design of the backbone of the administered oligomer. Specifically, the backbone should contain internucleoside linkages that are stable in vivo and should be structured such that the oligomer is resistant to endogenous nucleases, such as nucleases that attack the phosphodiester linkage. At the same time, the oligomer must also retain its ability to hybridize to the target DNA or RNA. (Agarwal, K. L. et al., *Nucleic Acids Res* (1979) 6:3009; Agarwal, S. et al., *Proc Natl Acad Sci USA* (1988) 85:7079.) In order to ensure these properties, a number of modified oligonucleotides have been constructed which contain alternate internucleoside linkages. Several of these oligonucleotides are described in Uhlmann, E. and Peyman, A., *Chemical Reviews* (1990) 90:543–584. Among these are methylphosphonates (wherein one of the phosphorous-linked oxygens has been replaced by methyl); phosphorothioates (wherein sulphur replaces one of these oxygens) and various amidates (wherein $NH_2$ or an organic amine derivative, such as morpholidates or piperazidates, replace an oxygen). These substitutions confer enhanced stability, for the most part, but suffer from the drawback that they result in a chiral phosphorous in the linkage, thus leading to the formation of $2^n$ diastereomers where n is the number of modified diester linkages in the oligomer. The presence of these multiple diastereomers considerably weakens the capability of the modified oligonucleotide to hybridize to target sequences. Some of these substitutions also retain the ability to support a negative charge and the presence of charged groups decreases the ability of the compounds to penetrate cell membranes. There are numerous other disadvantages associated with these modified linkages, depending on the precise nature of the linkage.

It has also been suggested to use carbonate diesters. However, these are highly unstable, and the carbonate diester link does not maintain a tetrahedral configuration exhibited by the phosphorous in the phosphodiester. Similarly, carbamate linkages, while chiral, confer trigonal symmetry and it has been shown that poly dT having this linkage does not hybridize strongly with poly dA (Coull, J. M., et al., *Tet Lett* (1987) 28:745; Stirchak, E. P., et al.,*J Org Chem* (1987) 52:4202.

WO 91/15500, published Oct. 17, 1991, teaches various oligonucleotide analogs in which one or more of the internucleotide linkages are replaced by a sulfur based linkage typically sulfamate diesters which are isosteric and isoelectric with the phosphodiester.

WO 89/12060, published Dec. 14, 1989, similarly discloses linkages containing sulfides, sulfoxides, and sulfones.

WO 86/05518, published Sep. 25, 1986, suggests a variant of stereoregular polymeric 3',5' linkages.

U.S. Pat. No. 5,079,151 to Lampson et al., discloses a msDNA molecule of branched RNA linked to a single strand DNA via a 2',5' phosphodiester linkage.

Commonly owned, pending U.S. patent application Ser. No. 690,786, filed Apr. 24, 1991, the entirety of which is incorporated by notice, describes modified linkages of the formula —Y'CX'$_2$Y'— wherein Y' is independently O or S and wherein each X' is a stabilizing substituent and independently chosen. Amide-containing linkages disclosed in commonly owned, pending U.S. patent application Ser. No. 07/889,736, filed May 28, 1992, S. Swaminathan, et al inventors, the entirety of which application is incorporated herein by reference, are also suitable for incorporation into oligomers containing one or more of the linkages disclosed herein.

Modifications of oligomers that enhance their affinity for target molecules will generally improve the therapeutic potential for those compounds. Previous approaches to improve binding affinity for complementary nucleic acids have centered primarily on (i) covalent linkage of intercalating agents to oligomers (Asseline, U., et al., *Proc Natl Acad Sci* (1984) 81:3297–3401), (ii) introduction of modified bases to form more stable base pairs (Inoue, H. et al., *Nucl Acids Res* (1985) 13:7119) and (iii) altering the charge characteristics of oligomer internucleotide linkages (Letsinger, R. L. et al., *J Am Chem Soc* (1988) 110:4470). Morpholino-type internucleotide linkages are described in U.S. Pat. No. 5,034,506 and in some cases give rise to an increased affinity of the oligomer for complementary target sequences.

Commonly owned pending U.S. patent applications Ser. No. 07/763,130, filed Sep. 20, 1991, and Ser. No. 07/690, 786 disclose modified oligonucleotides having modified nucleoside linkages which are capable of strong hybridization to target RNA and DNA.

That disclosure suggests that 3',5' internucleoside linkages are especially appropriate since the resulting oligonucleotides are stable in vivo, resistant to endogenous nucleases, and are able to hybridize to target nucleotide sequences. The structure of the oligonucleotide backbone suggests that 3',5' linkage is optimal for a phosphodiester linkage in view of the steric size of the phosphodiester group and the related bond lengths, angles, and torsions involved. Although a phosphodiester should be suitable for the 2',5' linkage since the O2'—P, P—O5' bond lengths, angles, and torsions are all appropriate, the steric bulk of the phosphodiester is too large for the space available between the 5' sugar (2' and 3' atoms) and the 3' sugar (O4' and C5'). Our discovery of the 2',5' linkage and its characteristics is based on modeling studies that both (i) predicted such linkages in a binding-competent oligonucleotide and (ii) defined the range of molecular characteristics such linkages could assume without loss of binding competence. Binding competence, as used herein, refers to either Watson-Crick pairing with single-stranded DNA or single-stranded RNA or to Hoogsteen pairing (Beal, P. A. et al., *Science* (1991) 251:1360–1363) with duplex nucleic acids including duplex DNA or duplex RNA.

Although space available for the 2',5' linkage has more stringent steric restraints upon it than does the space for the 3',5' linkage, there are fewer restrictions with regard to bond lengths, angles and the like. Because of this, the 2',5' linkage is fundamentally different from the 3',5' linkage. This restraint has been experimentally verified in that 2',5' phosphodiesters have been found not to be suitable for efficient hybridization (Kierzek, R. et al., *Nucl Acids Res* (1992) 20:1685–1690). However, the 2',5' linkages of this invention do not have the steric bulk of a phosphodiester but do fall within the range of requirements for bond length, angles, and torsion placed upon a linkage in that position. Consequently, our linkages are quite suitable and, in some cases, superior to 3',5' phosphodiester linkages.

The therapeutic potential of oligomers is generally enhanced by modifications that increase oligomer uptake by cells or reduce the rate of metabolism by cells or serum. Such modifications include (i) reduced oligomer charge, (ii) increased stability toward nuclease activity, and (iii) increased lipophilicity of the oligomer. oligomers having modified internucleotide linkages as described in the invention exhibit sequence-specific binding to complementary single stranded and duplex target sequences.

The present invention provides an internucleoside linkage which is resistant to nuclease digestion, and which is stable under physiological conditions, and which can be neutral or positively charged so as to enhance cell permeation. U.S. patent application Ser. No. 07/868,487 filed Apr. 14, 1992, the entire disclosure of which is incorporated herein by reference, describes modified oligomers that efficiently enter cytoplasm by passive diffusion. The linkages described herein are generally compatible with such permeation competent oligomers. Both nuclease stability and enhanced cellular permeation are important considerations for the development of oligonucleotide analogs that are intended to be used as therapeutic agents that function by binding to specific DNA or RNA (mRNA, hnRNA, etc.) sequences. Such specific target sequence binding underlies their therapeutic efficacy by interfering with the normal biological function of nucleic acid sequences associated with pathological conditions. Furthermore, the linkages can be achiral and thus do not lead to the problem of multiple diastereomers in the resulting compounds.

SUMMARY OF THE INVENTION

The present invention is based on the construction of novel oligonucleotides containing modified backbone linkages which linkages are also referred to as modified internucleoside linkages. These oligonucleotides are stable in vivo, resistant to endogenous nucleases and are able to hybridize to target nucleotide sequences.

In one embodiment, the present invention is directed to a modified oligonucleotide or derivative thereof, wherein the modification comprises substitution, for one or more phosphodiester linkages between 2' and 5' position adjacent nucleosides, with a two to four atom long internucleoside linkage wherein at least one of the atoms making up the internucleoside linkage is selected from nitrogen, oxygen and sulfur, with the remainder being carbon.

In another embodiment, the subject invention is directed to an oligomer of the formula:

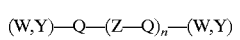

or a derivative thereof, where each

Y =

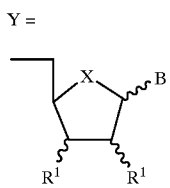

I

W =

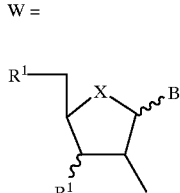

II

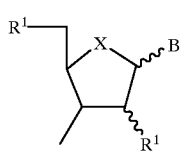

III

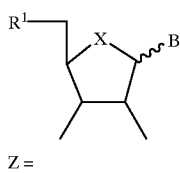

IV

Z =

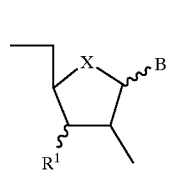

V

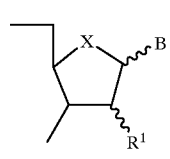

VI

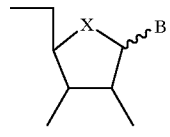

VII where X is S, O, $CH_2$, CHF or $CF_2$;

$R^1$ independently is —O-alkyl ($C_1$–$C_{12}$), —S-alkyl ($C_1$–$C_{12}$), H, OH, $OCH_3$, $SCH_3$, $OC_3H_5$ (O-allyl), $OC_3C_7$(O-propyl), $SC_3H_5$, or F and where $R^1$ is on a terminal group of the oligomer, $R^1$ may additionally be $PO_3^{-2}$ or a blocking group selected from a dimethoxytrityl (DMT) moiety, a monomethoxytrityl (MMT) moiety, H-phosphonate ($OPO_2H$), methylphosphonate ($OPO_2CH_3$) or phosphoramidite;

B is independently a purine or pyrimidine residue or an analogous residue, and

Q is independently
  a phosphodiester analog or
  a two to four atom long internucleoside linkage wherein at least one of the atoms making up the internucleoside linkage is selected from nitrogen, oxygen or sulfur, with the remainder being carbon; but no two adjacent atoms are oxygen and, for three atom linkages, no 3 adjacent atoms are all nitrogen or all oxygen or all sulfur and n is 1–100, preferably 2–28,
  but where each Q and each Z in each mer (n) is independently selected.

The designation (W, Y) means that either W or Y is linked to Q at the indicated positions. In preferred embodiments, a maximum of 20% of the linkages give rise to inversion of oligomer polarity. Linkages that invert polarity occur when there is a 5' to 5',3' to 2' or 3', or 2' to 3' or 2' linkage between adjacent nucleoside residues. The preferred linkage type for the majority of linkages in most oligomers is thus 3' or 2' to 5'. When X is $CH_2$ or CHF, the material may be produced according to published procedures (Otvos, L. et al. *Tet Letters* (1987) 28:6381–6384; Divakar, K. L. et al *J. Chem Soc Perkin Trans I* (1982) 1625; *J. Chem Soc., Perk. Trans. I* (1991) 2373–2377).

In preferred embodiments structure VII is included in oligomers as a nucleoside linked to an adjacent nucleoside through a riboacetal linkage. In other embodiments where VII is not linked via a riboacetal linkage, circular or branched oligomers may be obtained which are useful in oligonucleotide based therapies or diagnosis applications (Kool, E. T., *J Am Chem Soc* (1991) 113:6265–6266).

Oligomers are conveniently produced from dimers or trimers as synthons for solid phase or solution phase synthesis using standard methods known in the art.

In yet other embodiments, the invention is directed to methods for treating diseases mediated by the presence of a nucleotide sequence which comprise administering to a subject in need of such treatment an amount of the above modified oligonucleotides capable of specifically binding the nucleotide sequence effective so to inactivate the nucleotide sequence.

A feature of linkages wherein oxygen is located at the 2' position is enhanced stability of the glycosidic bond with the heterocycle. Such linkages are included in the group of preferred linkages described in detail below.

It has been found that oligomers containing these internucleotide linkages efficiently bind complementary single-stranded and double-stranded nucleic acid sequences. Triple helix structures were formed under physiological salt conditions. Unmodified control oligomers were less efficient at forming triple helices under the same conditions. Thus, oligomers of the present invention are generally characterized as containing one or more 2',5' or related linkages. The analogs may be utilized in oligomers that contain additional modifications of other nucleotides that comprise the oligomer. An exemplary list of such modifications include oligomers where (i) one or more nucleotide residue is modified at the 2' position, (ii) one or more crosslinking moieties have been incorporated, (iii) switchback linkers have been incorporated as described in copending U.S. application Ser. No. 07/559,958, incorporated herein by reference, (iv) other substitute internucleotide linkages have been included and (v) base analogs that facilitate duplex or triplex formation, such as 8-oxo-$N^6$-methyladenine, 5-propynyluracil, 5-propynylcytosine or 7-deazaxanthine have been included. One or more of such modifications may advantageously be incorporated into a given oligomer depending upon target nucleic acid sequences.

These and other embodiments of the present invention will readily occur to those of ordinary skill in the art in view of the disclosure herein.

BRIEF DESCRIPTION OF THE FIGURES

FIG. 1 shows the synthesis of a three atom long linkage with a nitrogen at the 5' end.

FIG. 2 shows the synthesis of a three atom long linkage with a nitrogen at the 2' end.

FIG. 3 depicts the synthesis of a three atom long linkage with a nitrogen in the middle.

FIG. 4 depicts the formation of a four atom long linkage with oxygen at the 2' end and nitrogen at the 5' end.

FIG. 5 shows the formation of a four atom long linkage with nitrogen at the 2' end and oxygen at the 5' end.

FIG. 6 depicts the formation of a two atom long linkage with nitrogen at the 5' end.

FIG. 7 shows the formation of a two atom long linkage with nitrogen at the 2' end.

FIG. 8 shows the formation of three different three atom long linkages with sulfur at the 2' end.

FIG. 9 depicts the formation of three different two atom long linkages with sulfur at the 2' end.

FIG. 10 shows the synthesis of three different two atom long linkages with sulfur at the 5' end.

FIG. 11 depicts the synthesis of a two atom long linkage with oxygen at the 2' end.

FIG. 12 depicts the formation of a three atom long linkage with oxygen at the 5' end.

FIG. 13 shows the formation of several three atom long linkages with derivatized nitrogen at the 2' end.

FIG. 14 shows the synthesis of a three atom long linkage containing nitrogen at the 2' end and oxygen at the 5' end.

FIG. 15 shows the formation of a three atom long linkage with sulfur at the 2' end.

FIG. 16 shows the formation of a three atom linkage having a nitrogen atom at the 2' end and an oxygen-bearing carbon atom at mid-linkage and oxygen at the 5' end.

FIG. 17 shows the formation of a three atom linkage having an oxygen atom at the 2' end and an oxygen-bearing carbon atom at mid linkage and nitrogen at the 5' end and also a linkage having an oxygen at the 2' end and a sulfur at the 5' end and a carbon midlinkage.

FIGS. 18 and 19 show the formation of certain feedstocks such as compound 1 in FIG. 1 and compound 10 in FIG. 2 suitable for synthesis of the desired oligomers of this invention.

DESCRIPTION OF THE INVENTION

Figure 1:
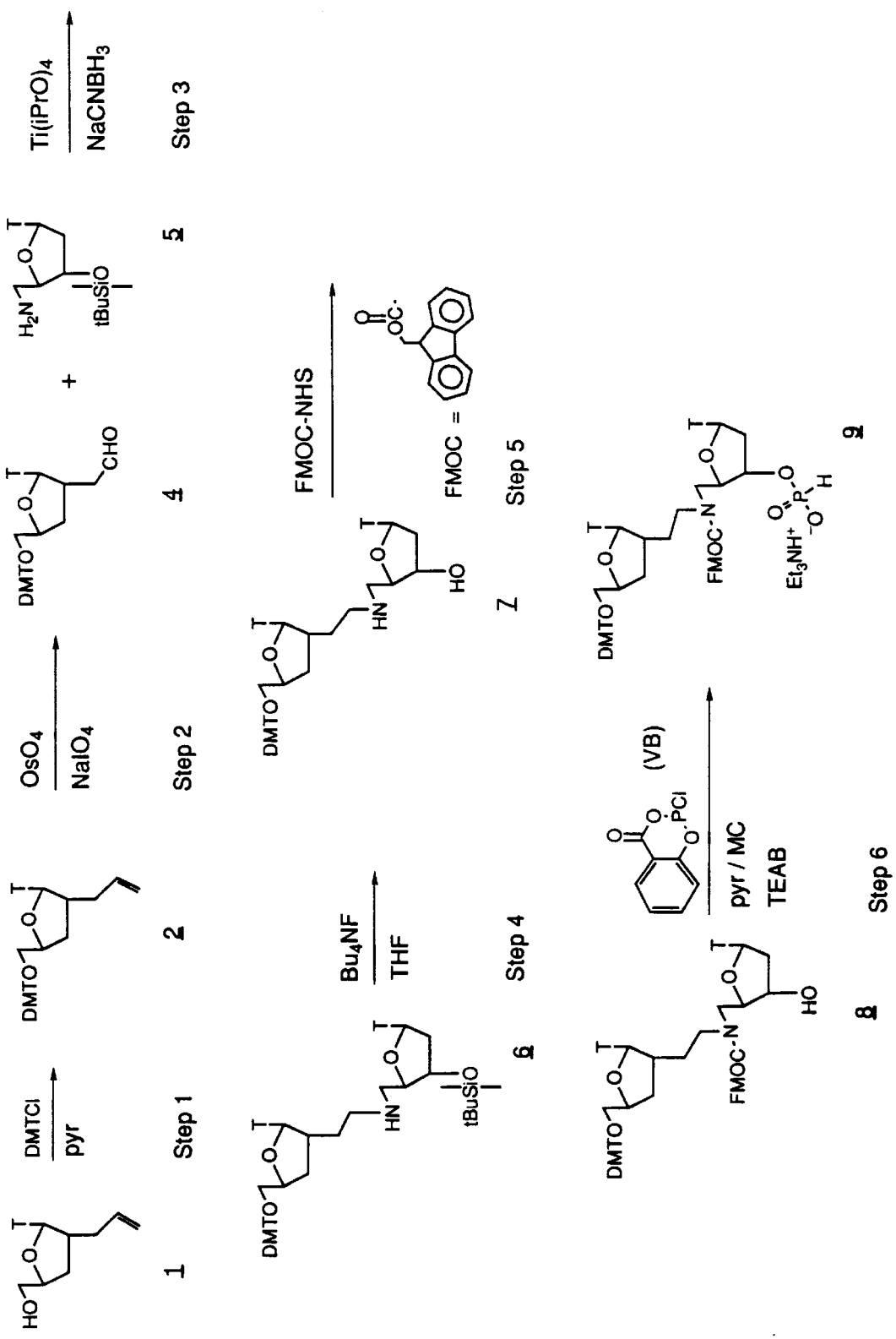
FIGS. 1 through 17 are depictions of chemical reaction sequences usable for synthesizing internucleoside linkages of the present invention. More specifically.

The practice of the present invention will employ, unless otherwise indicated, conventional techniques of chemistry, molecular biology, biochemistry, protein chemistry, and recombinant DNA technology, which are within the skill of the art. Such techniques are explained fully in the literature. See, e.g., *Oligonucleotide Synthesis* (M. J. Gait ed. 1984); *Nucleic Acid Hybridization* (B. D. Hames & S. J. Higgins eds. 1984); Sambrook, Fritsch & Maniatis, *Molecular Cloning: A Laboratory Manual*, Second Edition (1989); and the series *Methods in Enzymology* (S. Colowick and N. Kaplan eds., Academic Press, Inc.).

A. Definitions

In describing the present invention, the following terms will be employed, and are intended to be defined as indicated below.

As used herein, oligonucleotide-based therapy refers to administration or in situ generation of DNA or RNA oligomers or their derivatives which bind specifically to a target nucleic acid sequence. The binding may be by conventional base pair complementarity, or, for example, in the case of binding to DNA duplexes, through specific interactions in the major groove of the double helix. In general, "antisense" refers to the range of techniques generally employed under this description in the art for binding to single-stranded RNA, and includes any therapy which relies on specific binding to oligonucleotide sequences. Similarly, another use of oligonucleotide-based therapy is through the generation of oligomers ("aptamers") which bind specifically to proteins thereby interfering with their function. Still another use of oligonucleotide-based therapy is direct replacement with one strand of a duplex nucleic acid ("D-looping"). Efficient D-looping requires the use of oligomers having a high binding affinity for their complementary target sequences.

As used herein "oligonucleotide" or "oligomer" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base. Oligonucleotide or oligomer, as used herein, is intended to include (i) compounds that have one or more furanose moieties that are replaced by furanose derivatives or by any structure, cyclic or acyclic, that may be used as a point of covalent attachment for the base moiety, (ii) compounds that have one or more phosphodiester linkages that are either modified, as in the case of phosphoramidate or thioate linkages, or completely replaced by a suitable linking moiety as in the case of formacetal or riboacetal linkages, and/or (iii) compounds that have one or more linked furanose-phosphodiester linkage moieties replaced by any structure, cyclic or acyclic, that may be used as a point of covalent attachment for the base moiety as described in commonly owned pending U.S. application Ser. No. 07/889,736, filed May 28, 1992, the entire disclosure of which is incorporated herein by reference and in Nielsen, P. E. et al (*Science* (1991) 254:1497–1500. Thus, the term "oligonucleotide," as used herein, includes compounds such as a formacetal linked "thymidine" dimer (e.g., 5' T—O—$CH_2$—O—T 3'), which does not necessarily contain a phosphorus atom.

"Nucleoside" refers to a sugar or derivative thereof, as described further below, carrying a purine, pyrimidine, or analogous forms thereof, as defined below, but lacking a linking sequence such as a phosphodiester analog or a modified internucleoside linkage. By "5'" nucleoside is meant the nucleoside which provides the 5' carbon coupling point to the linker. The "5'" end of the linker couples to the 5' nucleoside. The "2'" end of the linker joins to the 2' position on the next nucleoside. If a modified nucleoside is present which does not precisely include a 2' and/or a 5' carbon, it is to be understood that this "2'" and "5'" terminology will be used by analogy.

"Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc). These additional moieties may be (but need not be) derivatized through the modified backbone linkage as part of the linkage itself. For example, intercalators, such as acridine may be linked through an —R'—$CH_2$—R'— attached through any available —OH or —SH, e.g., at the terminal 5',2' or 3' position of RNA or DNA, the 2',5', or 3' positions of RNA, or an OH or SH engineered into the 5 position of pyrimidines, e.g., instead of the 5 methyl of cytosine, a derivatized form which contains —CH₂CH₂CH₂OH or —CH₂CH₂CH₂SH in the 5 position. A wide variety of substituents may be attached, including those bound through conventional linkages. Accordingly, the indicated —OH moieties in the oligomer of formula (1) may be replaced by phosphonate groups, protected by standard protecting groups, or activated to prepare additional linkages to other nucleotides, or may be bound to the conjugated substituent. The 5' terminal OH is conventionally phosphorylated; the 3'-OH or OH substituents at the 2' terminus may also be phosphorylated. The hydroxyls may also be derivatized to standard protecting groups. In addition, specifically included are the 2'- or 3'-derivatized forms of the nucleotide residues disclosed in commonly owned, copending U.S. application Ser. No. 425,857, as well as the formacetal/ketal type linkages disclosed in commonly owned, copending U.S. patent application Ser. No. 557,957, both incorporated herein by reference in their entirety. Synthesis of DNA oligomers and nucleosides with 2' modifications has been described for 2' fluoro compounds (Uesugi, S. et al., *Biochemistry* (1981) 20:3056–3062; Codington, J. F. et al., *J Organic Chem* (1964) 29:564–569; Fazakerley, G. V. et al., *FEBS Letters* (1985) 182:365–369), 2'-O-allyl compounds (OC₃H₅) (Sproat, B. S. et al., *Nucleic Acids Res* (1991) 19:733–738 and 2'-azido compounds (Hobbs, J. et al., *Biochemistry* (1973) 12:5138–5145). These derivatives are also specifically included and the chemistry is applicable to both 2' and 3' position.

Specific modifications that are contemplated for oligomers described in the present invention include moieties that permit duplex strand switching as described in commonly owned, pending PCT patent application No. PCT/US90/06128, moieties such as $N^4,N^4$-ethanocytosine (aziridinylcytosine) that affect covalent crosslinking as described in commonly owned, pending U.S. patent application Ser. No. 640,654 and moieties such as the base analog 8-hydroxy-$N^6$-methyladenine, 6-aminocytosine or 5-propynyluracil that facilitate oligomer binding to duplex target nucleic acid as described in commonly owned, pending U.S. patent application Ser. Nos. 643,382 and 799,824. All applications cited herein are incorporated herein by reference.

By "phosphodiester analog" is meant an analog of the conventional phosphodiester linkage

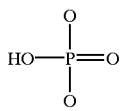

as well as alternative linking groups. These alternative linking groups include, but are not limited to embodiments wherein the HO—P=O(P(O)OH) is replaced with P(S)S, P(O)S, P(O)NR"₂, P(O)R", P(O)OR'", wherein R" is H or alkyl (1–6C) and R'" is alkyl (1–6C). The linkage listed below are suitable for Q, formacetal and riboacetal linkages. Suitable riboacetal and formacetal linkages are disclosed in copending application having Ser. Nos. 07/690,786; 07/763,130, and 07/806,710, all of which are incorporated by notice, and include formacetal linkages such as:

3'-thioformacetal (—S—CH₂—O—), formacetal (—O—CH₂—O—),

3'-amino (—N—CH₂—CH₂—),

3'-thioketal (—S—C(R⁸)₂—O—), and ketal —O—C (R⁸)₂—O— where $R^8$ is CH₂F or, when both $R^8$ are taken together with the atom to which they are attached, form a 4-membered ring or a 6-membered ring where $(R^8)_2$ is —CH₂—$X^1$—CH₂—, or
—CH₂—CH₂—$X^1$—CH₂—CH₂—;

and wherein $X^1$ is selected from the group consisting of S, SO, SO₂, O, CF₂, CHF, NH, NMe, NEt, NPr.

Suitable riboacetal linkages include members of the group:

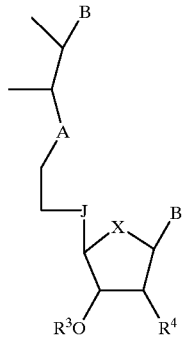

IX

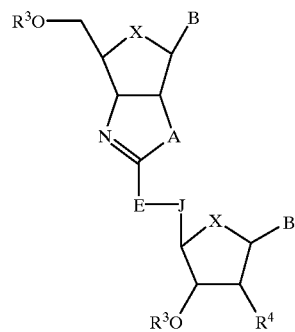

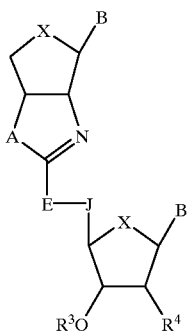

XI

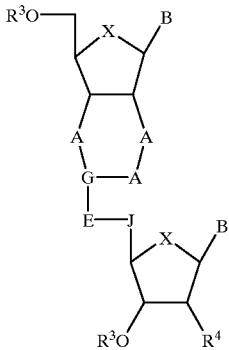

XII

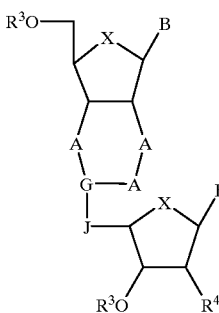

XIII

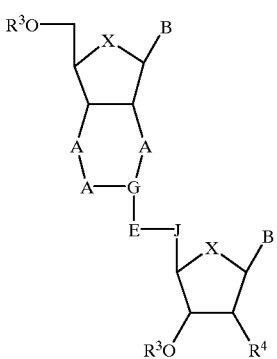

XIV

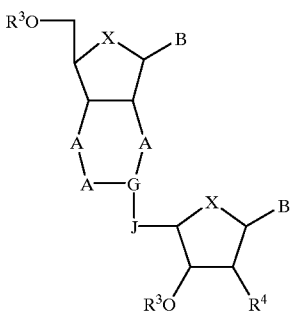

XV

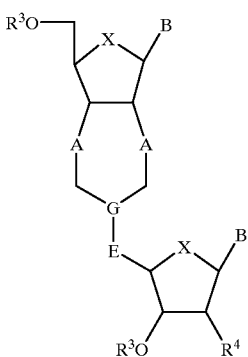

where $R^3$ is independently H, $PO_3^{-2}$ or a suitable blocking group such as a dimethoxytrityl (DMT) moiety, a monomethoxytrityl (MMT) moiety, H-phosphonate ($OPO_2H$), methylphosphonate ($OPO_2CH_3$) or phosphoramidite; $R^4$ is selected from the group consisting of H, OH, F, $OCH_3$, $O_2CH_5$, $OCH_2CHCH_2$ (O-allyl, $OC_3H_5$), $OC_3H_7$ (O-propyl), $SCH_3$, $SC_2H_5$, $SCH_2CHCH_2$ (S-allyl, $SC_3H_5$), and $SC_3H_7$ (S-propyl). Methylphosphoramidite and β-cyanoethylphosphoramidite are preferred phosphoramidite groups. B is a purine or pyrimidine base or an analogous form thereof; X is independently selected from the group consisting of O, S, $CH_2$, $CF_2$ and CFH; A is independently selected from the group consisting of O, S, SO, $SO_2$, $CH_2$, CO, $CF_2$, CS, NH and $NR^5$ wherein $R^5$ is lower alkyl (including methyl, ethyl, propyl, isopropyl, butyl and isobutyl) with the proviso that adjacent A are not both O; E is selected from the group consisting of O, S, $CH_2$, CO, $CF_2$, CS, NH and $NR^5$; J is selected from the group consisting of O, S, $CH_2$, CO, $CF_2$ and CS; G is selected from the group consisting of CH, N, CF, CCl, and $CR^7$ wherein $R^7$ is lower alkyl (including methyl, ethyl, propyl, isopropyl, butyl and isobutyl) or lower fluoroalkyl (1–4C, 1–5F). Bases (B) that are preferred are adenine, thymine, guanine, cytosine, 8-oxo-$N^6$-methyladenine, $N^4$, $N^4$-ethanocytosine, pseudo-isocytosine and 5-methylcytosine, 5-propynyluracil, 5-propynylcytosine, 7-deazaxanthine and 7-deazaguanine.

Not all phosphodiester analogs in the same oligomer need be identical, the only requirement being that at least one of these linkages is a modified internucleoside linkage as described herein. Also included in the definition of "derivatives" are substances wherein the conventional ribose sugar is replaced with heterocyclic compounds such as morpholine.

"Analogous" forms of purines and pyrimidines are those generally known in the art, many of which are used as chemotherapeutic agents. An exemplary but not exhaustive list includes 4-acetylcytosine, 8-hydroxy-$N^6$-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, xanthine, hypoxanthine, 5-iodouracil, 5-iodocytosine, 5-ethyluracil, 5-propynyluracil, 5-bromovinyluracil, 8-azaadenine, 7-deazaadenine, 6-chloropurine, 3-deazaguanine, 7-deazaguanine, 3-deazaadenine, 6-aminocytosine, 6-aminouracil, 5-methylcytosine, 6-amino-5-methylcytosine, 6-thioguanine, 6-amino-5-propynylcytosine, 6-amino-5-alkylcytosine, 5-methoxyuracil, 2-methylthio-N6-isopentenyladenine, methylester, uracil-5-oxyacetic acid, 5-methyl-2-thiouracil, 2-thiouracil, 4-thiouracil, 5-methyluracil, uracil-5-oxyacetic acid, pseudouracil, queosine, 2-thiocytosine, and 2,6-diaminopurine. Particularly preferred analogs are 5-methylcytosine (abbreviated herein as "Cme"), 5-propynyluracil, 7-deazaxanthine, pseudoisocytosine, and 6-aminocytosine.

The invention is directed to new compounds which are useful in oligonucleotide-based therapies and intermediates in their production, as well to methods to synthesize these compounds and their intermediates. In general, the invention compounds show enhanced stability with respect to nucleases by virtue of their modified linkages, as well as enhanced ability to permeate cells.

In a modified oligonucleotide of this invention, at least one of the phosphodiester groups included within the Qs of Formula 1 is substituted by the modified 2'–5' internucleoside linkages described herein. Desirably, multiple phosphodiester linkages in the unmodified oligonucleotides are substituted by the modified backbone linkages described herein. One modified internucleoside linkage may be used repeatedly in this structure, or, if desired a variety of modified internucleoside linkages may be used. Though it is preferred that these substituent linkages be non-chiral in nature to enhance the ability to hybridize, useful compounds of the invention can include those where chiral forms are used.

Preferred modified internucleoside linkages include the structures for Q shown in Table 1.

TABLE 1

—N(R⁶)—CH₂—

—CH₂—N(R⁶)—

—N(R⁶)—N(R⁶)—

—N(R⁶)—CH₂—CH₂—

—CH₂—N(R⁶)—CH₂—

—CH₂—CH₂—N(R⁶)—

—N(R⁶)—N(R⁶)—CH₂—

—N(R⁶)—CH₂—N(R⁶)—

—CH₂—N(R⁶)—N(R⁶)—

—N=C(NH₂)—N(R⁶)—

—O—CH₂—
—CH₂—O—
—O—CH₂—CH₂—
—CH₂—O—CH₂—
—CH₂—CH₂—O—
—O—CH₂—O—
—S—CH₂—O—
—O—CH₂—S—
—S—CH₂—S—

—S—CH₂—S(=O)(=O)—

—S—CH₂—
—CH₂—S—

—S(=O)—CH₂—

TABLE 1-continued

—S(=O)(=O)—CH₂—

—CH₂—S(=O)—

—CH₂—S(=O)(=O)—

—S—CH₂—CH₂—

—S(=O)—CH₂—CH₂—

—S(=O)(=O)—CH₂—CH₂—

—CH₂—CH₂—S(=O)(=O)—

—CH₂—S(=O)(=O)—CH₂—

—CH₂—S—CH₂—
—CH₂—CH₂—S—

—S(=O)—CH₂—S—

—S(=O)(=O)—CH₂—S(=O)(=O)—

—NR⁶—C(=O)—S—

—NR⁶—C(=S)—S—

—NR⁶—C(=S)—NR⁶—

—NR⁶—C(=O)—NR⁶—

—S—C(=O)—NR⁶—

TABLE 1-continued
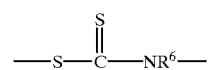
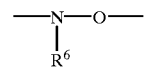
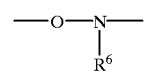
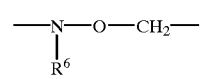
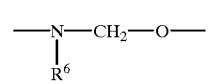
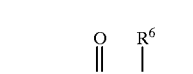
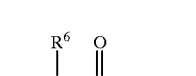
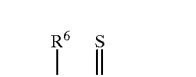
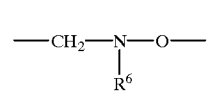
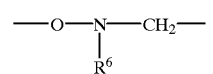
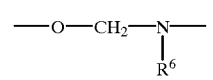
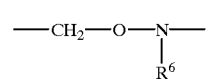
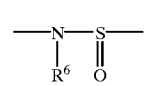
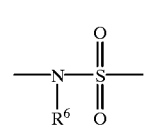
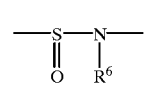
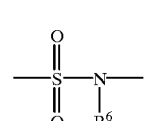
TABLE 1-continued
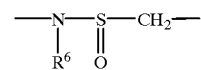
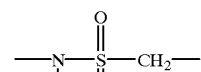
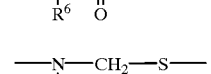
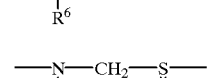
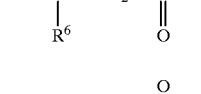
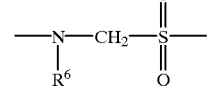
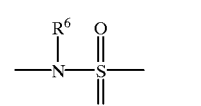
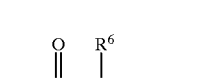
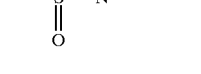
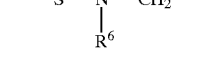
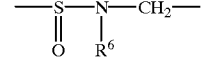
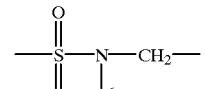
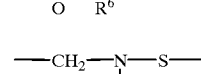
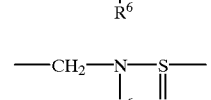

TABLE 1-continued

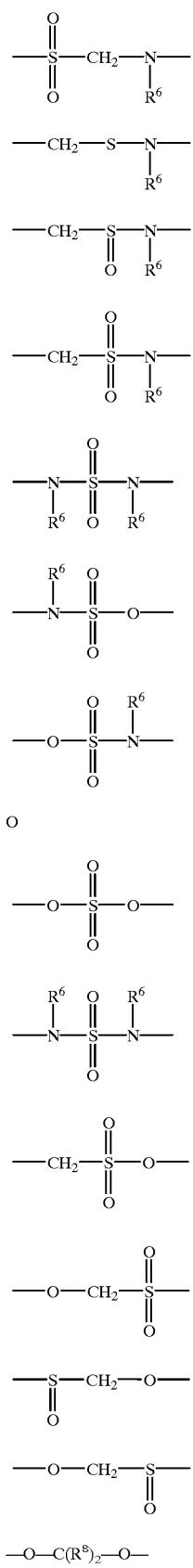

TABLE 1-continued

—S—C(R$^8$)$_2$—O—, and
—O—C(R$^8$)$_2$—S—, wherein R$^6$ is H, lower alkyl, including methyl, ethyl, propyl and butyl, OMe, OH, heteroalkyl, or aryl; and wherein R$^8$ is CH$_2$F, or when both R$^8$ are taken together with the atom to which they are attached, form a 4-membered or 6-membered ring where (R$^8$)$_2$ is
—CH$_2$—X$^1$—CH$_2$—,
—(CH$_2$)$_2$—X$^1$—(CH$_2$)$_2$—; or
wherein X$^1$ is selected from the group consisting of NH, NMe, NEt, NPr, S, SO, SO$_2$, O, CF$_2$ and CHF.
Particularly preferred internucleoside linkages include

—S—CH$_2$—CH$_2$—    —S—CH$_2$—

—O—C(=S)—NR$^6$—    —O—CH$_2$—S—

—O—CH$_2$—O    —O—C(=O)—NR$^6$—

—CH$_2$—CH$_2$—S    —CH$_2$—S—

—NR$^6$—C(=S)—O—    —S—CH$_2$—O—

—NR$^6$—C(=O)—O.

It should be clear that the invention compounds are not limited to oligomers of homogeneous linkage type, and that alternating or randomly distributed phosphodiester analogs and the modified backbone linkages are contemplated. Since the oligomers of the invention can be synthesized one nucleotide residue at a time, each individual linkage, and the nature of each individual "B" substituent can be chosen at will.

The Q linkages should be stable. The extent to which the spectrum of substituents present in the Q linkages can be extended can readily be determined by simple assays of stability of the resulting product, and this determination, and a good deal of predictability of the tolerance of these linkages, is within the ordinary skill of the art.

It should further be noted that if Q, itself, contains a functional group, Q can be used to tether desired moieties useful as adjuncts in therapy, for example, intercalators or minor groove reactive materials, such as netropsin and its derivatives, anthramycin, quinoxaline antibiotics, actinomycin, and pyrrolo (1–4) benzodiazepine derivatives.

The oligomers of the invention may contain an arbitrary number of the modified internucleoside linkages of the invention. These may be identical to each other or different by virtue of the embodiments chosen for Q. Since the oligomers are prepared sequentially, any pattern of linkage types, base substituents, and carbohydrate residues may be used.

In some preferred embodiments, the modified internucleoside linkages alternate in a regular pattern. For example, one modified linker followed by two phosphodiester analog linkages followed by one modified linker, etc. Additional alternatives might include, for example, alternating linkages such as a modified linkage followed by a phosphodiester analog followed by a modified linkage followed by a phosphodiester analog, etc., so that there is a one-by-one alternation of the two types of linkages. A variety of regularly variant patterns is readily derived.

It is also clear that arbitrary modifications may be made to one or more of these carbohydrate residues; however, for the most part, the standard 2'–5' nucleotide linkage between ribosyl residues is most convenient. Where this is the case, further abbreviation of the structures may be used. For example, in standard DNA (or RNA) the sequences are generally denoted by the sequence of bases alone, such as, for example, ATG CGC TGA. In general, it is simply stated in advance whether this represents an RNA or DNA sequence. In the compounds of the invention, similar notation will be used for modifications of otherwise physiological DNA or RNA molecules but the phosphodiester linkages replaced by the modified backbone linkages will be noted in the structure. Thus, 5'-TCTCme(O—C(O)—NR)TCme(O—C(O)—NR)TCme(O—C(O)—NR)TCme(O—C(O)—NR)TTTT—2' indicates an oligonucleotide TCTCmeTCmeTCmeTCmeTTTT (the Cme denoting 5-methylcytosine) with four of the phosphodiester linkages replaced in the noted positions.

We have found in general that several chemical advantages appear to be inherent to the 2'–5' linkage series, at least when compared to the corresponding 3'–5' linkage series. These advantages provide the 2'–5' with significantly more flexibility. Specifically, the 3'-deoxy sugar is synthesized de novo to be appended to any aglycone of choice; therefore, one is not limited to modifications of naturally occurring nucleosides. Also, the presence of a 2'-acyl group on the sugar (compound #108, scheme #16) insures the formation of the β-anomer preferentially, in good yield, when appended via the Vorbruggen method (Niedballa, U. et al., *J Org Chem* (1974) 39:3654). If the corresponding 3'-acyl-2'-deoxy carbohydrate was subjected to the same conditions, a mixture of α- and β-anomers would be obtained.

Furthermore, the presence of a 2'-hydroxyl group or oxygen is also known to stabilize the glycosidic linkage. Studies (See, Michelson, A. M. in "The Chemistry of Nucleosides and Nucleotides," 1963, Academic Press, N.Y., p. 26–27, and Garrett, E. R., Mehta, P. J., *J. Am. Chem. Soc.*, 1972, 94, 8532) have shown that the 2'-deoxy nucleosides are 1000 times more susceptible to acid catalyzed deglycosylation when compared to the corresponding ribonucleoside. On the contrary, 3'-deoxy nucleosides are only 2–3 times less stable to acid-catalyzed deglycosylation when compared to the parent riboside. Therefore, the presence of the 2'-hydroxyl not only renders the nucleoside/tide more stable to synthetic conditions, but also allows access into nucleoside analogs containing a modified aglycone which otherwise would render the glycosidic bond too unstable for practical use.

B. Utility and Administration

Since the oligonucleotides of the invention are capable of significant single stranded or double stranded target nucleic acid binding activity to form duplexes, triplexes or other forms of stable association, these oligonucleotides are useful in diagnosis and therapy of diseases that are associated with expression of one or more genes such as those associated with viral infections due to say, HIV, HCMV, HSV or HPV. However, other therapeutic applications may also employ the oligomers to specifically inhibit the expression of genes that are associated with the establishment or maintenance of a pathological condition. Exemplary genes that may be targeted would encode adhesion molecules, receptor molecules or oncogenes that may be associated with inflammatory conditions, immune reactions or cancer, respectively. Diagnostic applications for the oligomers described herein include their use as probes for detection of specific sequences by any standard method.

In therapeutic applications, the oligomers are utilized in a variety of oligonucleotide-based therapies, e.g., for treatment of say, viral infections or malignant conditions. For such therapy, the oligomers can be formulated for a variety of modes of administration, including systemic, topical or localized administration. Techniques and formulations generally may be found in *Remington's Pharmaceutical Sciences*, Mack Publishing Co., Easton, Pa., latest edition. The oligomer active ingredient is generally combined with a carrier such as a diluent or excipient which may include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included. Dosages that may be used for systemic administration preferably range from about 0.01 mg/Kg to 50 mg/Kg administered once or twice per day. However, different dosing schedules may be utilized depending on factors such as (i) the potency of an individual oligomer at inhibiting the activity of its target gene, (ii) the severity or extent of a pathological disease state associated with a given target gene, or (iii) the pharmacokinetic behavior of a given oligomer. Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target gene sequences to which they specifically bind. Such diagnostic tests are conducted by hybridization through either double or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

Oligomer probes may also incorporate additional modifications such as altered internucleotide linkages that render the oligomer especially nuclease stable, and would thus be useful for assays conducted in the presence of cell or tissue extracts which normally contain nuclease activity. Oligonucleotides containing terminal modifications often retain their capacity to bind to complementary sequences without loss of specificity (Uhlmann et al., *Chemical Reviews* (1990) 90:543–584). As set forth above, the invention probes may also contain linkers that permit specific binding to alternate DNA strands by incorporating a switchback linker that permits such binding.

Incorporation of base analogs of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res* (1986) 14:9943).

In addition to their use in antisense, triple helix or aptamer therapies, the oligomers of the invention may also be applied as therapeutic or diagnostic agents that function by direct displacement of one strand in a duplex nucleic acid. Displacement of a strand in a natural duplex such as chromosomal DNA or duplex viral DNA, RNA or hybrid DNA/RNA is possible for oligomers with a high binding affinity for their complementary target sequences. Therapeutic applications of oligomers by this method of use, referred to herein as D-looping or "D-loop therapy" has not previously been possible because the affinity of natural DNA or RNA for its complementary sequence is not great enough to efficiently displace a DNA or RNA strand in a duplex. Therapeutic efficacy of oligomers that function by D-looping would result from high affinity binding to a complementary sequence that results in modulation of the normal biological function associated with the nucleic acid target. Types of target nucleic acids include but are not limited to (i) gene sequences including exons, introns, exon/intron junctions, promoter/enhancer regions and 5' or 3' untranslated regions, (ii) regions of nucleic acids that utilize secondary structure in order to function (e.g., the HIV TAR stem-loop element or tRNAs), (iii) nucleic acids that serve structural functions such as telomeres or centromeres and (iv) duplex regions that do not serve a known function. It is clear that oligomers may be synthesized with discrete functional domains wherein one region of an oligomer binds to a target by D-looping while an adjacent region binds a target molecule by say, forming a triple helix or binding as an aptamer to a protein. Alternatively, a D-looping oligomer may bind to each strand in a duplex by switching the strand to which the oligomer binds (i.e. by having one region of the oligomer that binds to one strand and another region that binds to the complementary strand). The controlling elements that dictate the mode of binding (i.e. triple helix or D-loop) are the sequence of the oligomer and the inherent affinity built into the oligomer. Base recognition rules in Watson-Crick duplex binding differ from those in Hoogsteen controlled triplex binding. Because of this, the oligomer base sequence can be used to dictate the type of binding rules an oligomer will utilize.

D-loop structures are formed in nature by enzyme-mediated processes (Harris, L. D. et al., *J Biol Chem* (1987) 262:9285–9292) or are associated with regions where DNA replication occurs (Jacobs, H. T. et al., *Nucl Acids Res* (1989) 17:8949–8966). D-loops that arise from the binding of oligomers may result from a one or two step process. Direct displacement of a target strand will give rise to a D-loop by a single binding event. However, D-looping may also occur by forming a triple helix which facilitates a strand displacement event leading to the D-loop.

In addition to the foregoing uses, the ability of the oligomers to inhibit gene expression can be verified in in vitro systems by measuring the levels of expression in recombinant systems.

It may be commented that the mechanism by which the specifically-binding oligomers of the invention interfere with or inhibit the activity of a target RNA or DNA is not always established, and is not a part of the invention. If the oligomer seeks, for example, a target mRNA, translation may be inhibited. In addition, by binding the target, the degradation of the mRNA message may be enhanced, or the further processing of the RNA may be inhibited. By formation of a triple helix, the transcription or replication of the subject DNA may be inhibited; furthermore, reverse transcription of infectious RNA or replication of infectious DNA is interfered with. It is also thought that the immune function may be modulated through physiological mechanisms similar to those induced by double-stranded RNA as exemplified by the "ampligen" system or similar to those used to suppress systemic lupus erythematosus. The oligomers of the invention are characterized by their ability to target specific oligonucleotide sequences regardless of the mechanisms of targeting or the mechanism of the effect thereof.

Finally, it is understood that the oligomers can be derivatized to a variety of moieties which include, intercalators, chelators, lipophilic groups, label, or any other substituent which modifies but does not materially destroy the oligomeric character of the backbone.

C. Synthesis of the Analogs

The oligomers of the invention which contain the modified internucleoside linkages can be synthesized using reactions known in the art of oligonucleotide derivative synthesis. See e.g. Flandor, J. and Yam, S. Y., *Tet Letts* (1990) 31:597–600; Mattson, R. J. et al., *J Org Chem* (1990) 55:2552–2554; Chung, C. K et al., *J Org Chem* (1989) 54:2767–2769.

Figure 2:
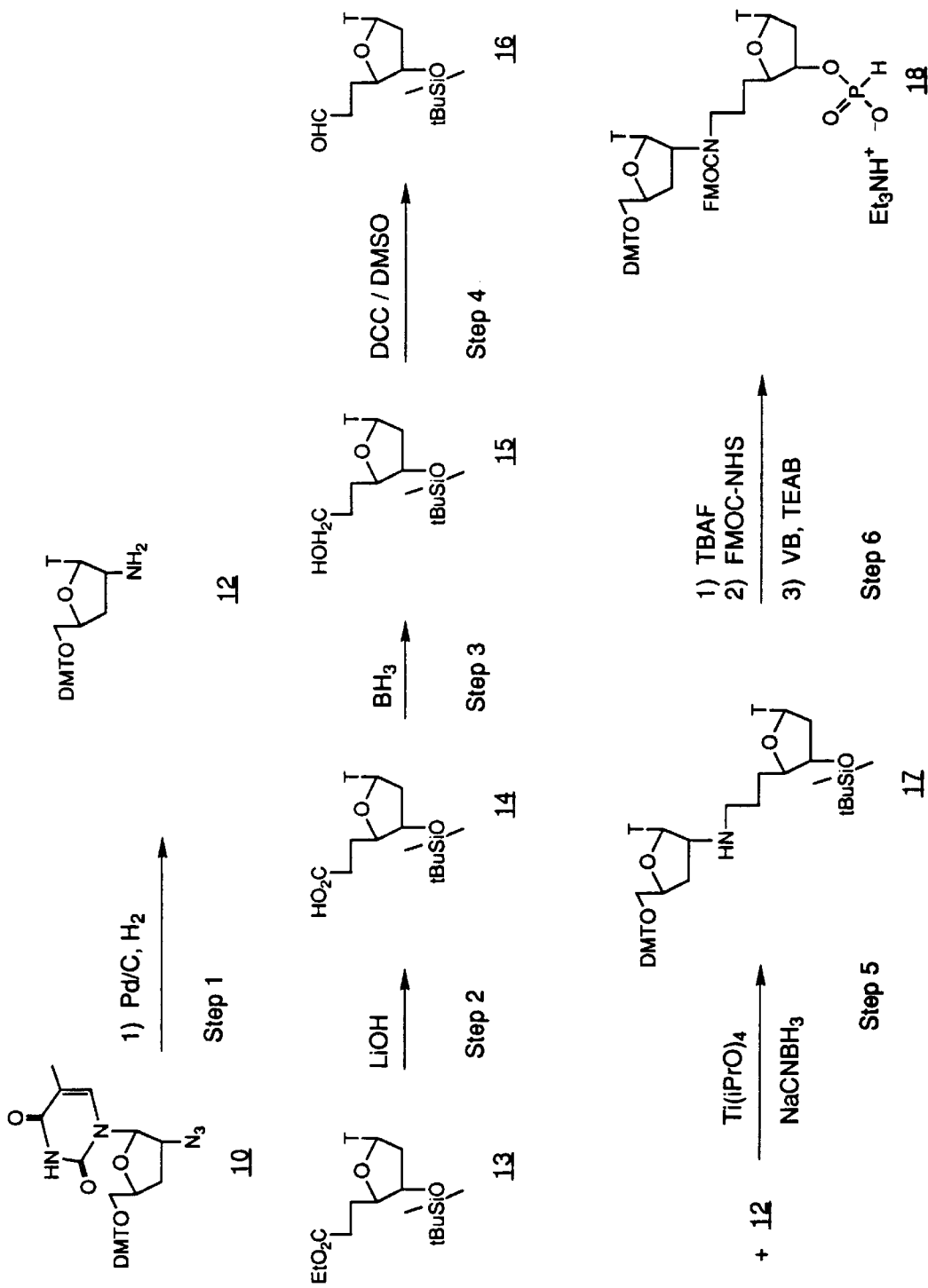
Figure 3:
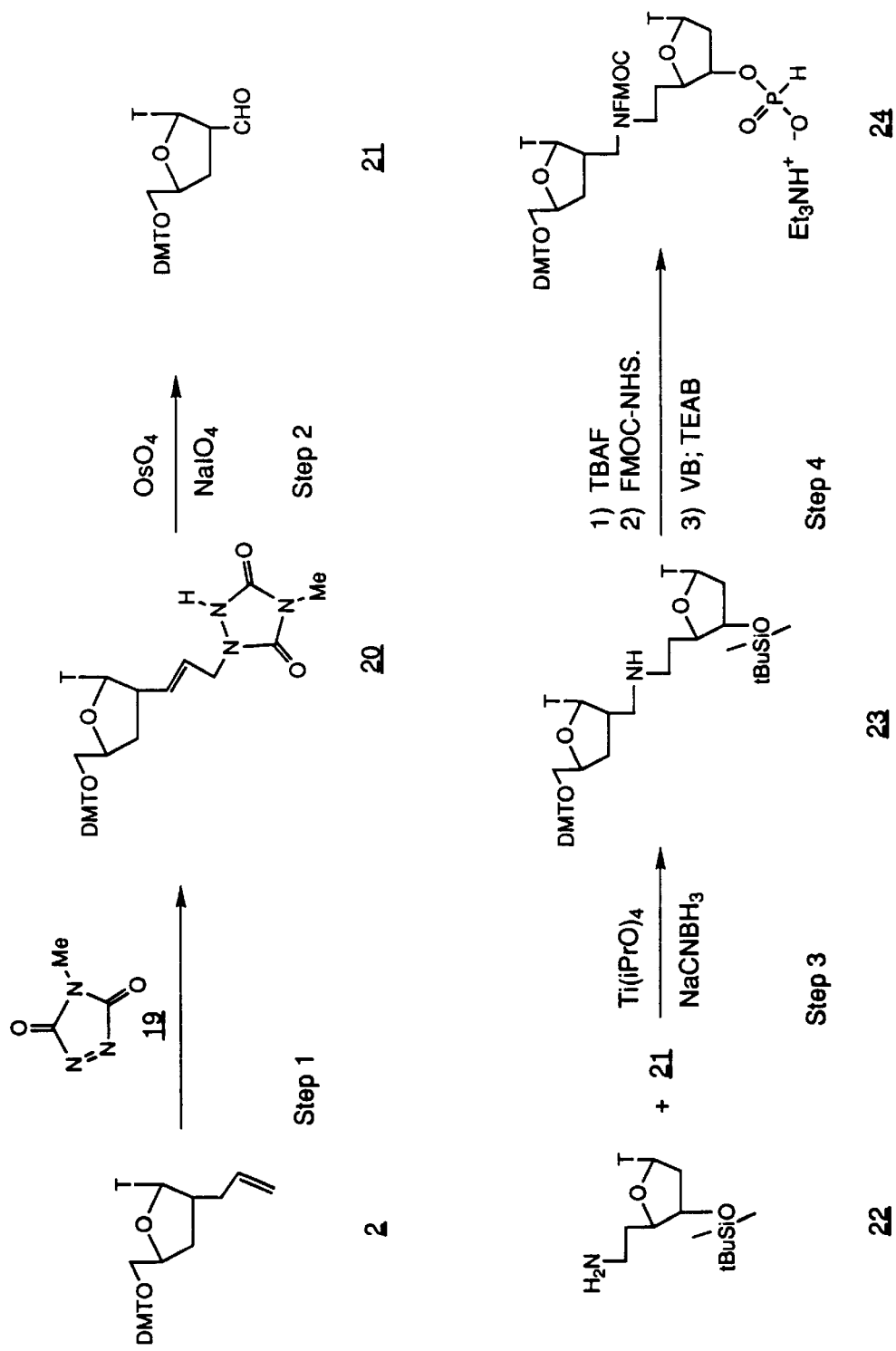
Figure 4:
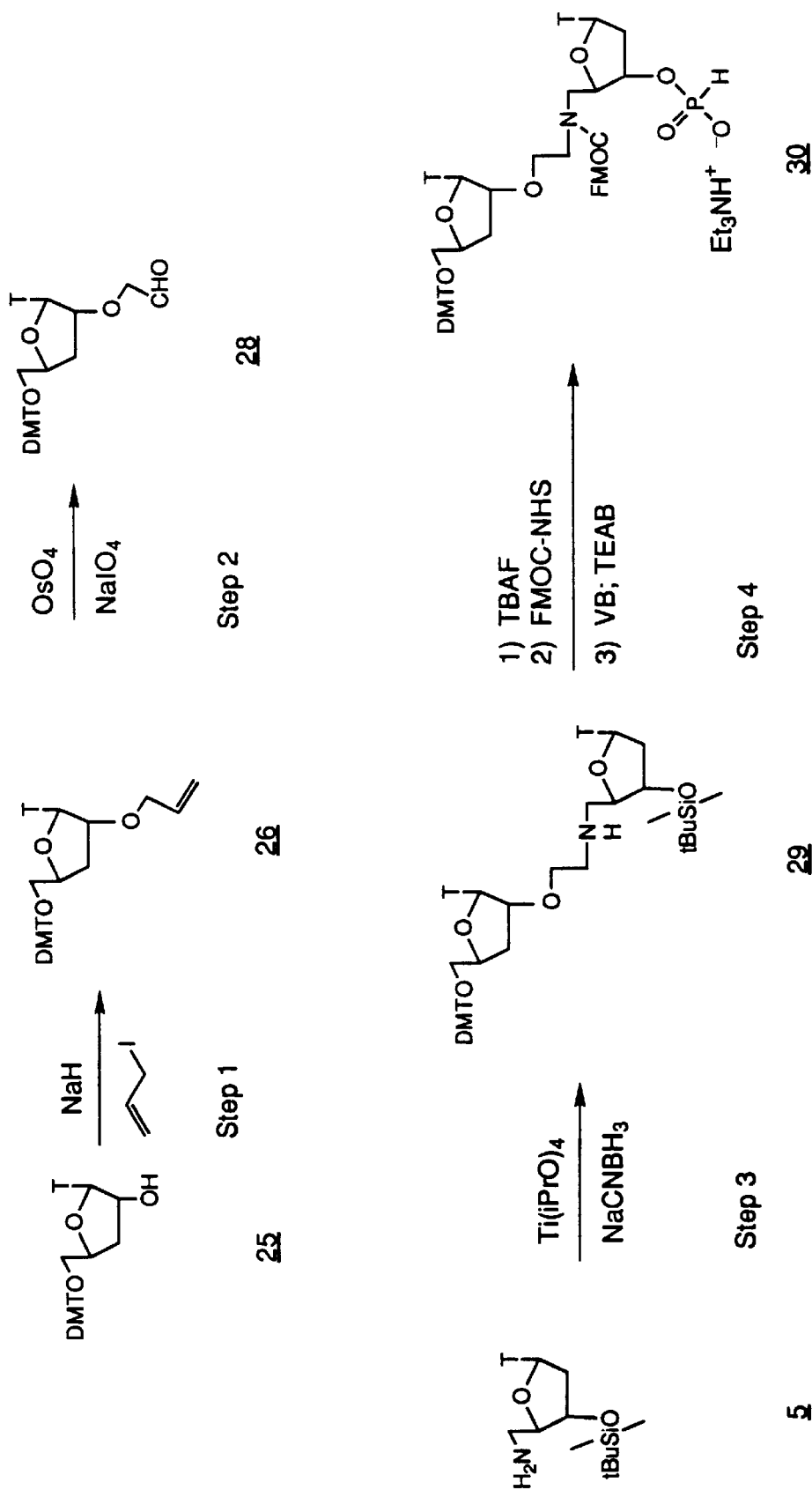
Figure 5:
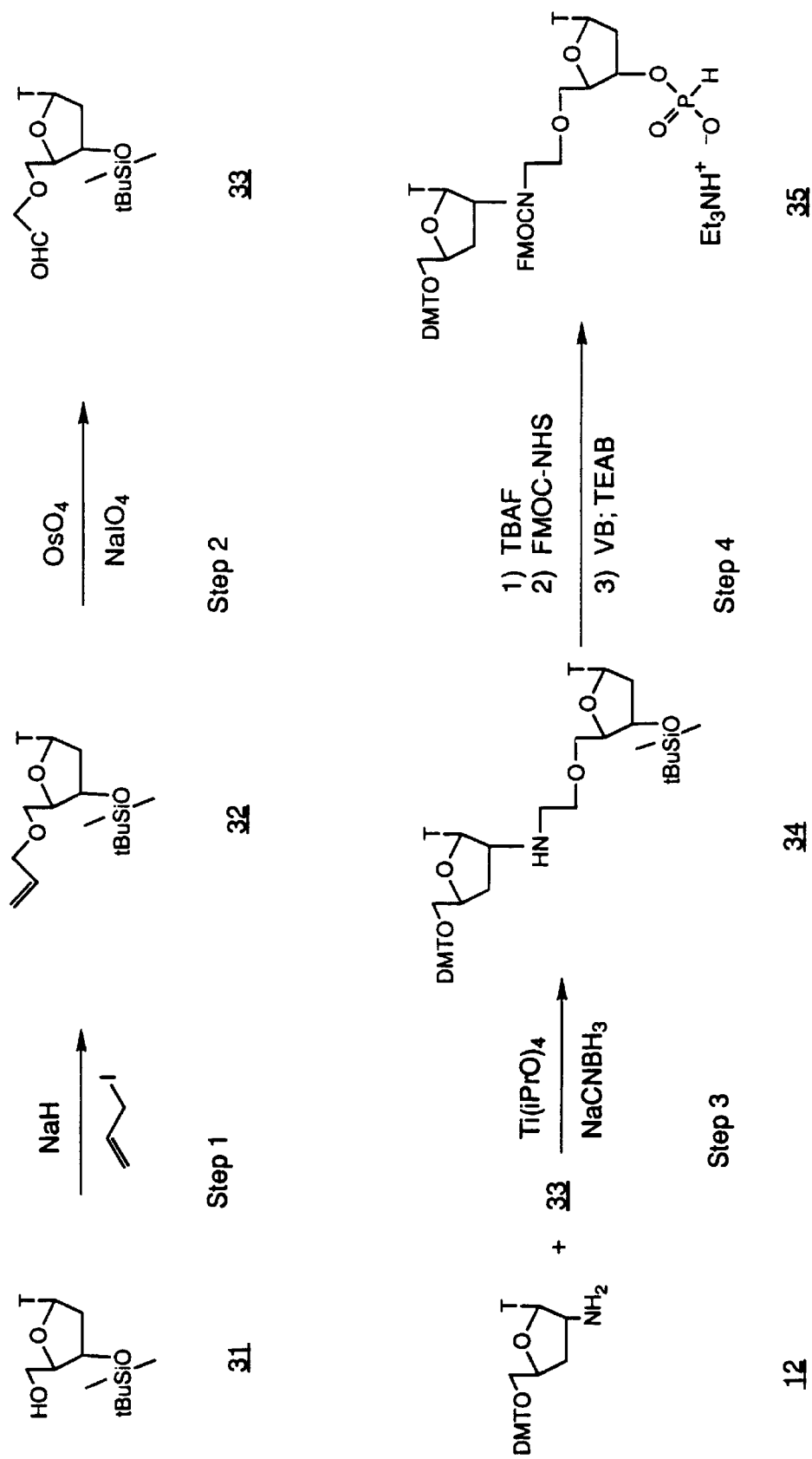
Figure 6:
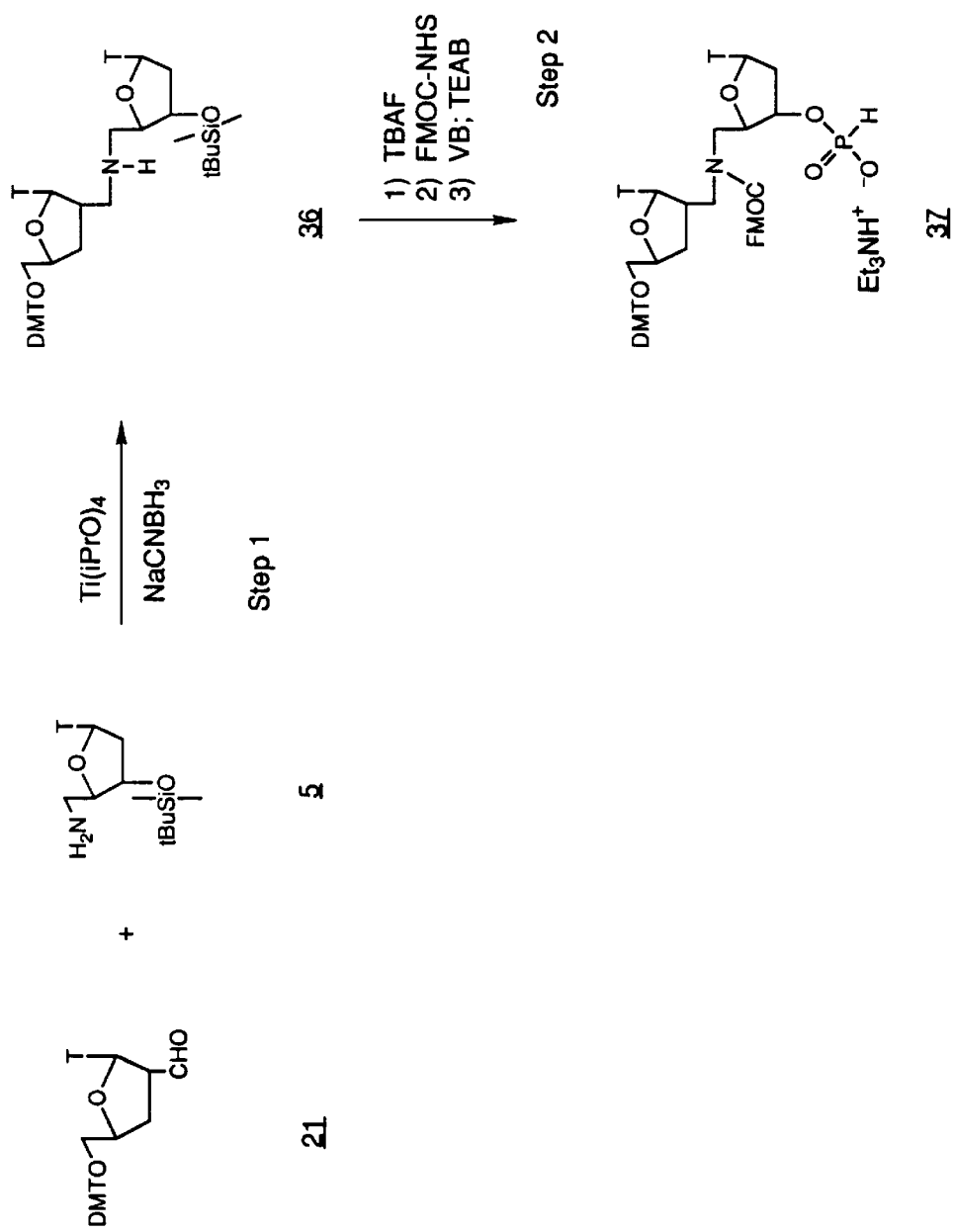
Figure 7:
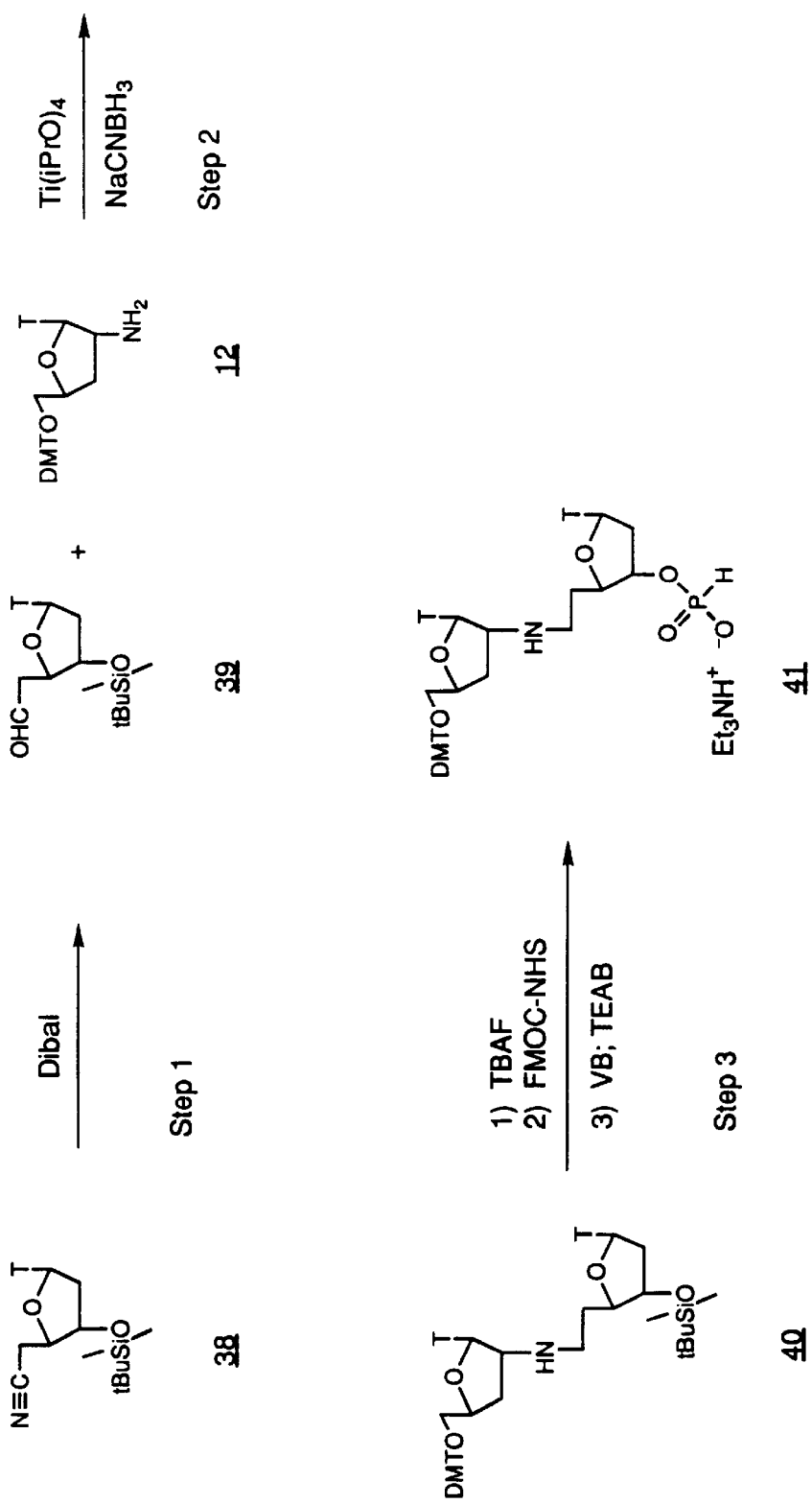
Figure 8:
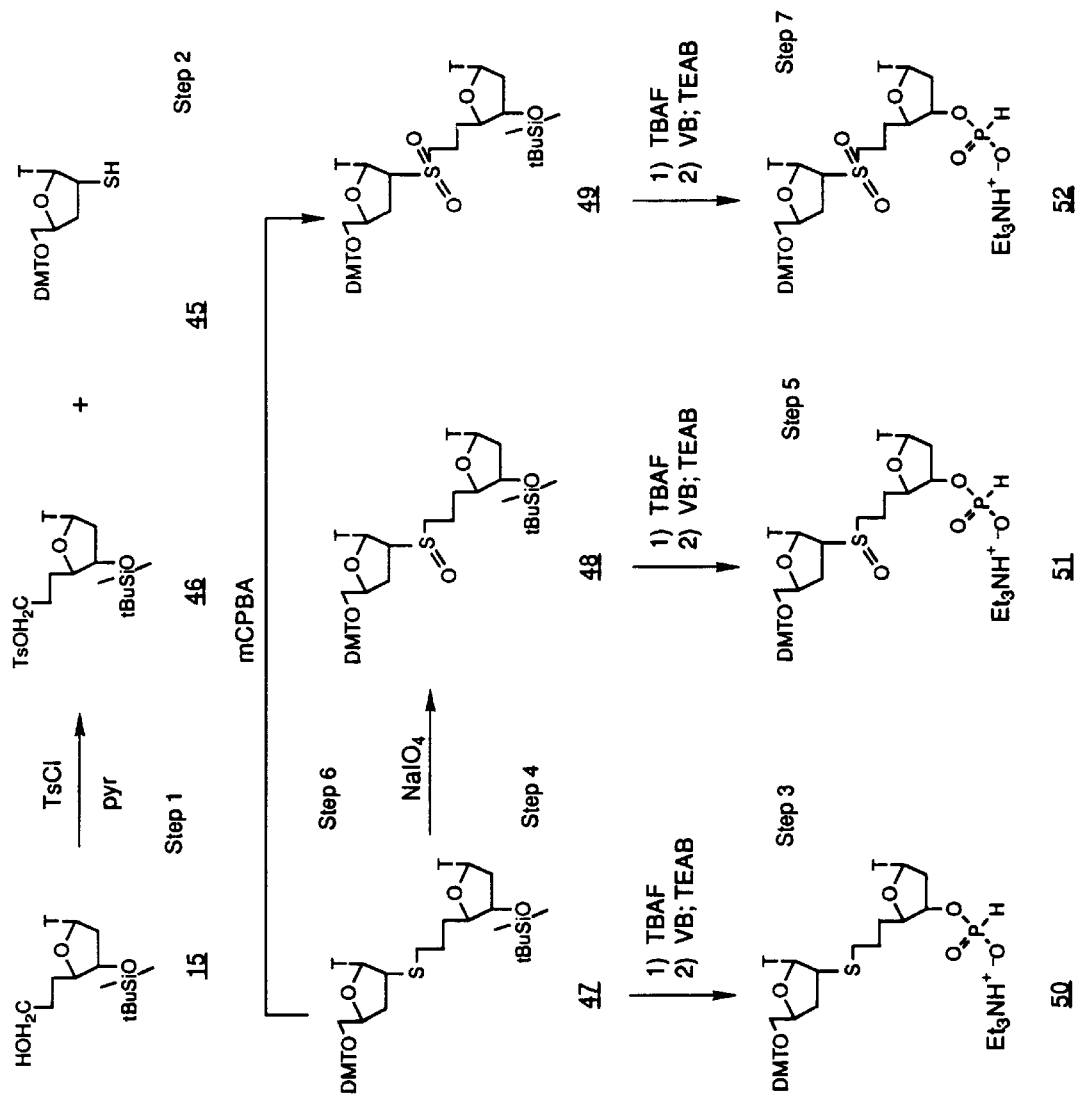
Figure 9:
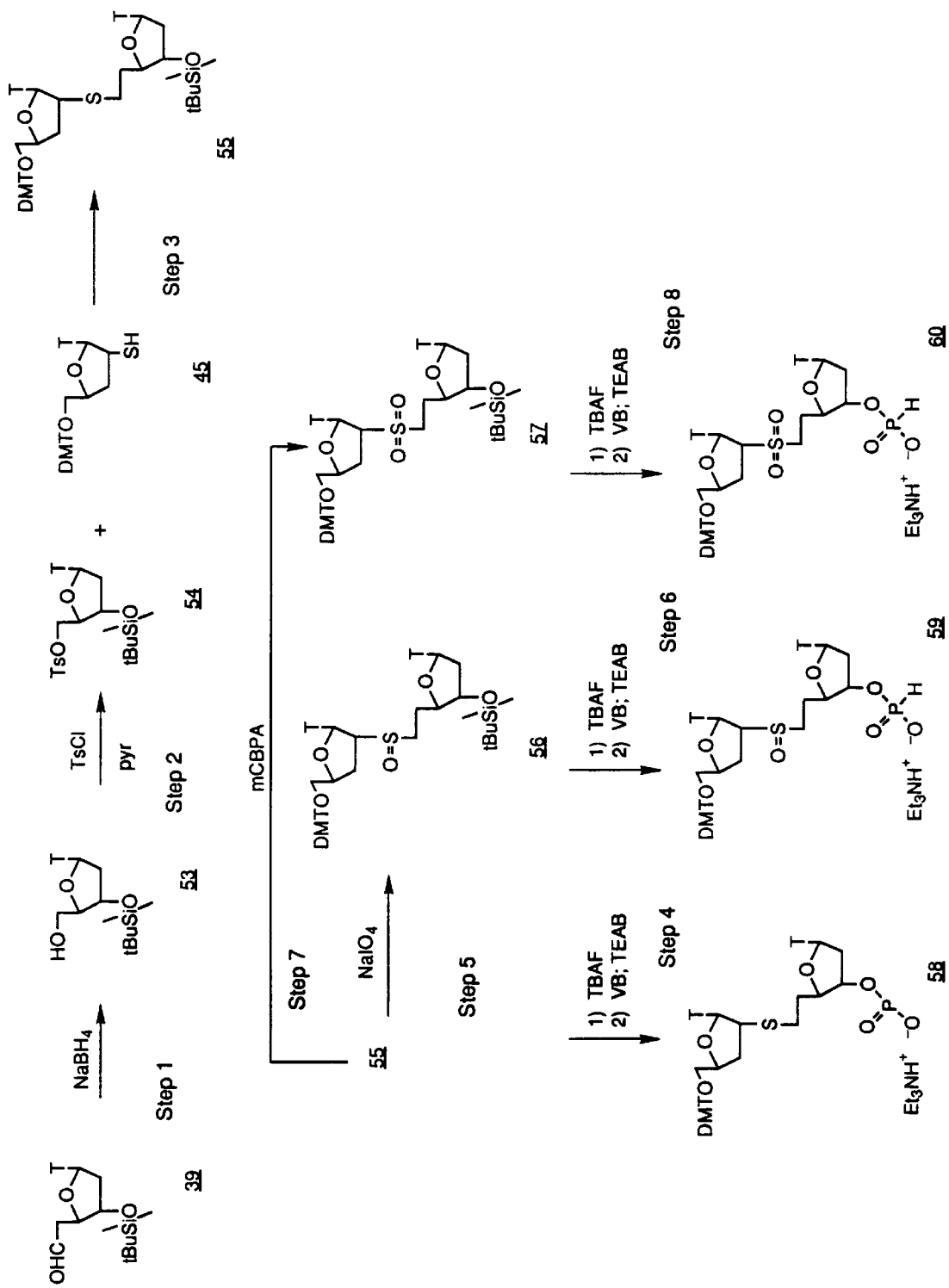
Figure 10:
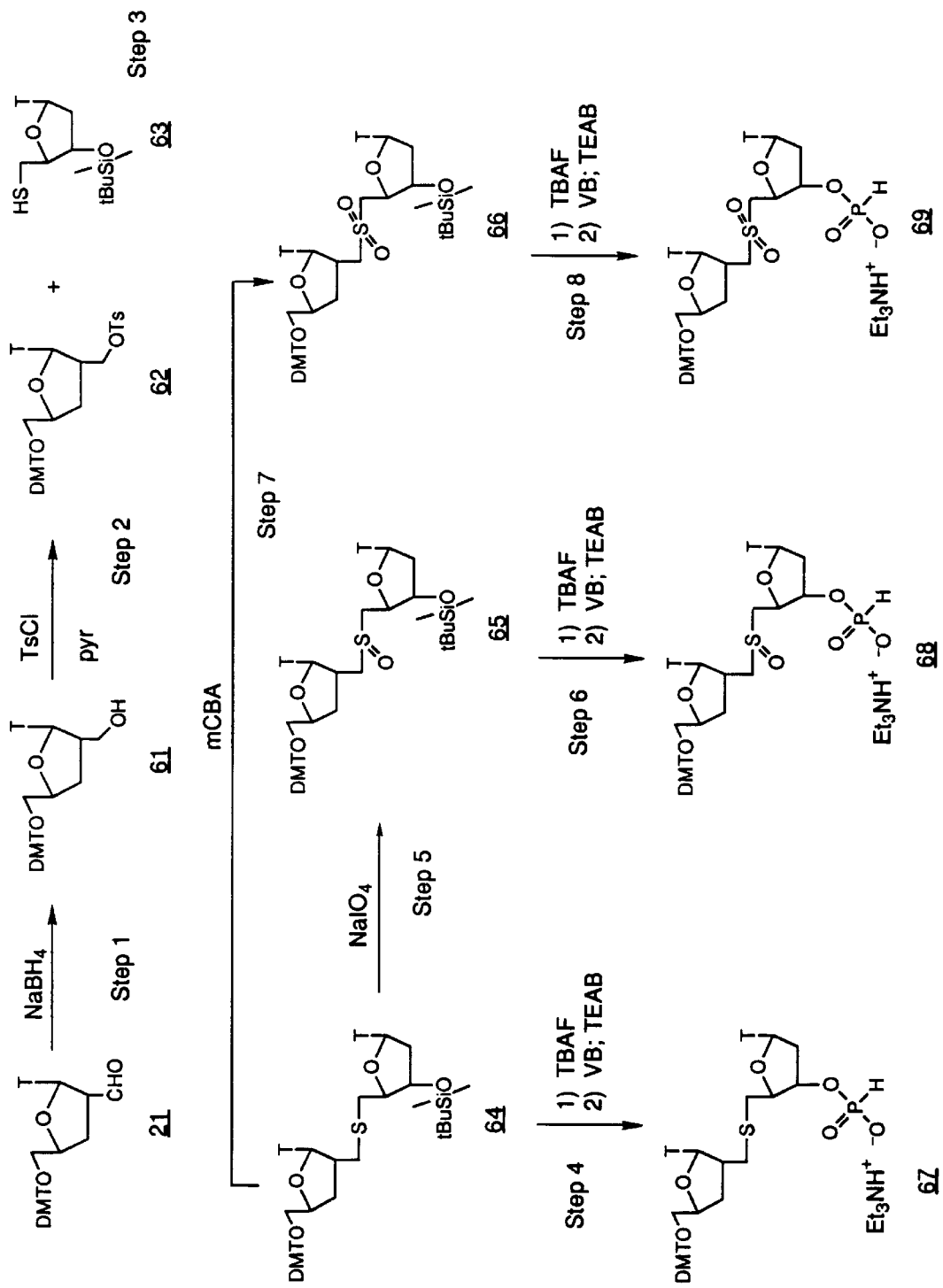
Figure 11:
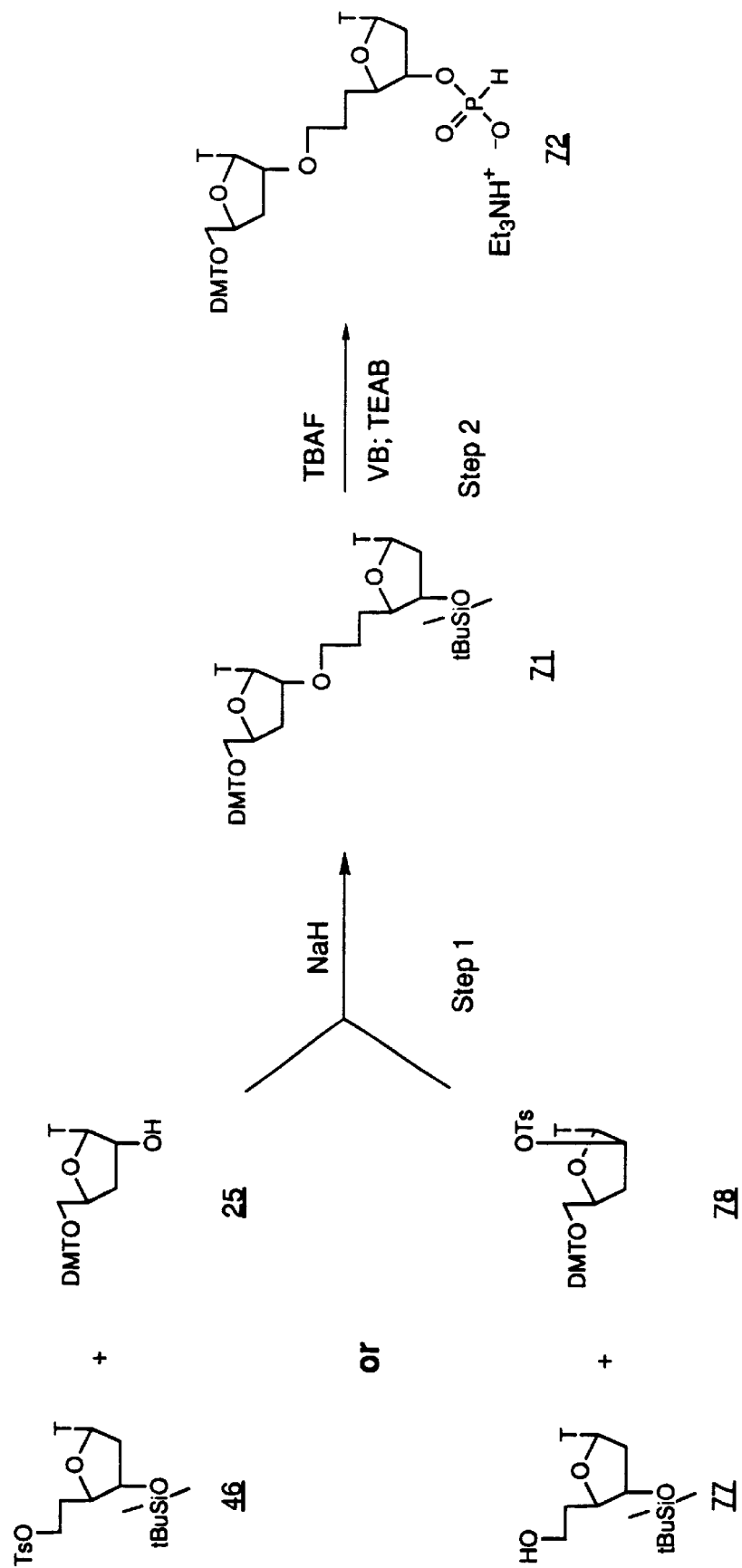
Figure 12:
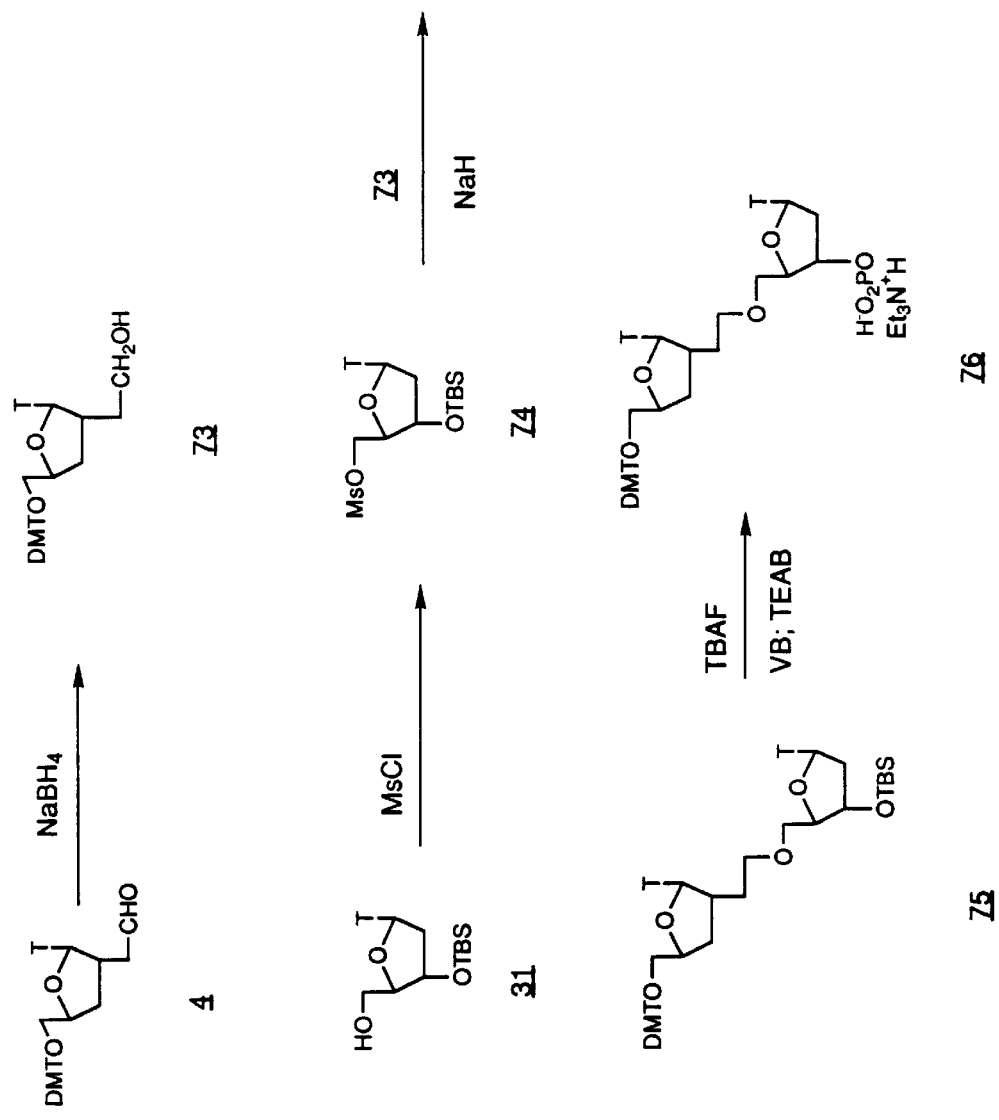
Figure 13:
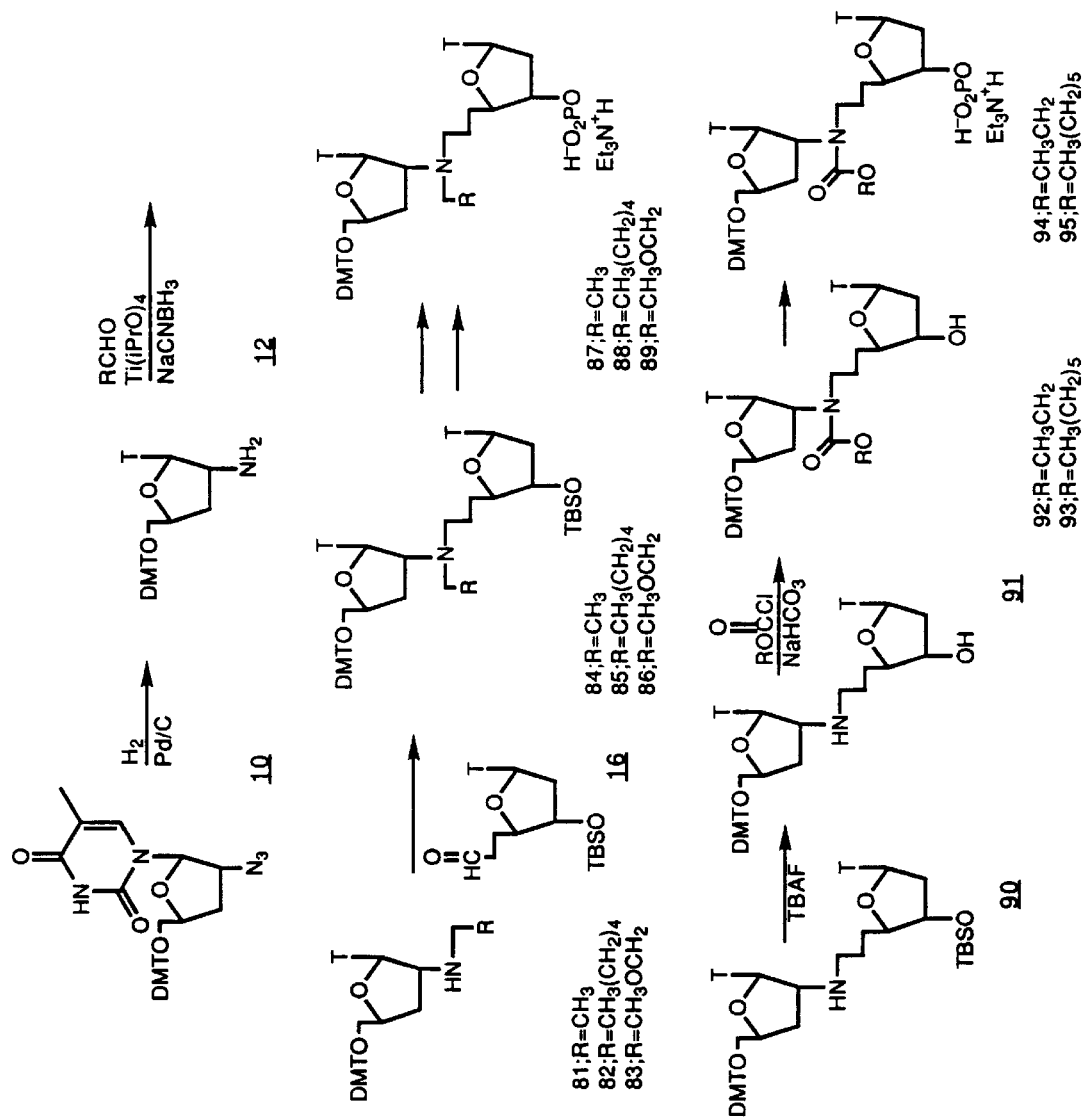
Figure 14:
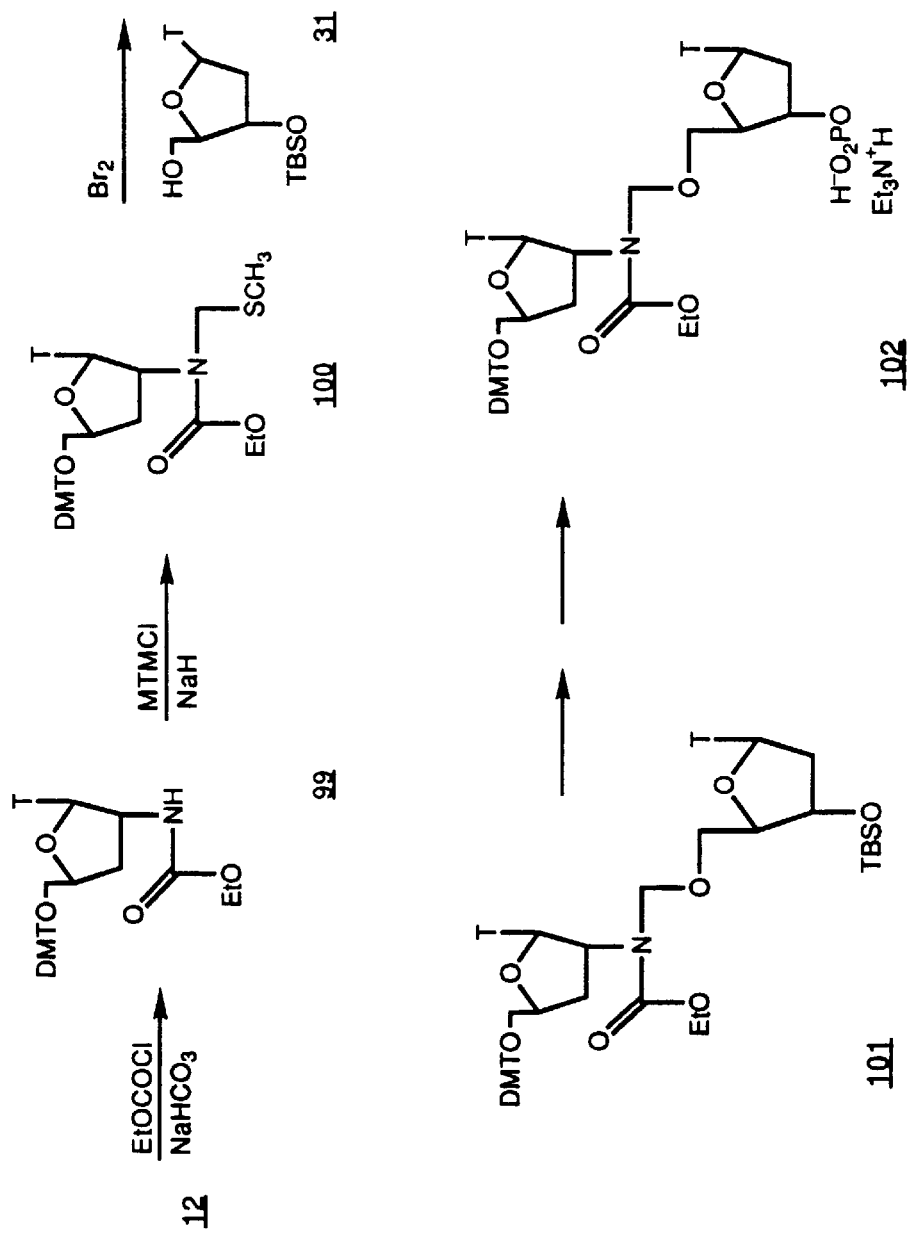
Figure 16:
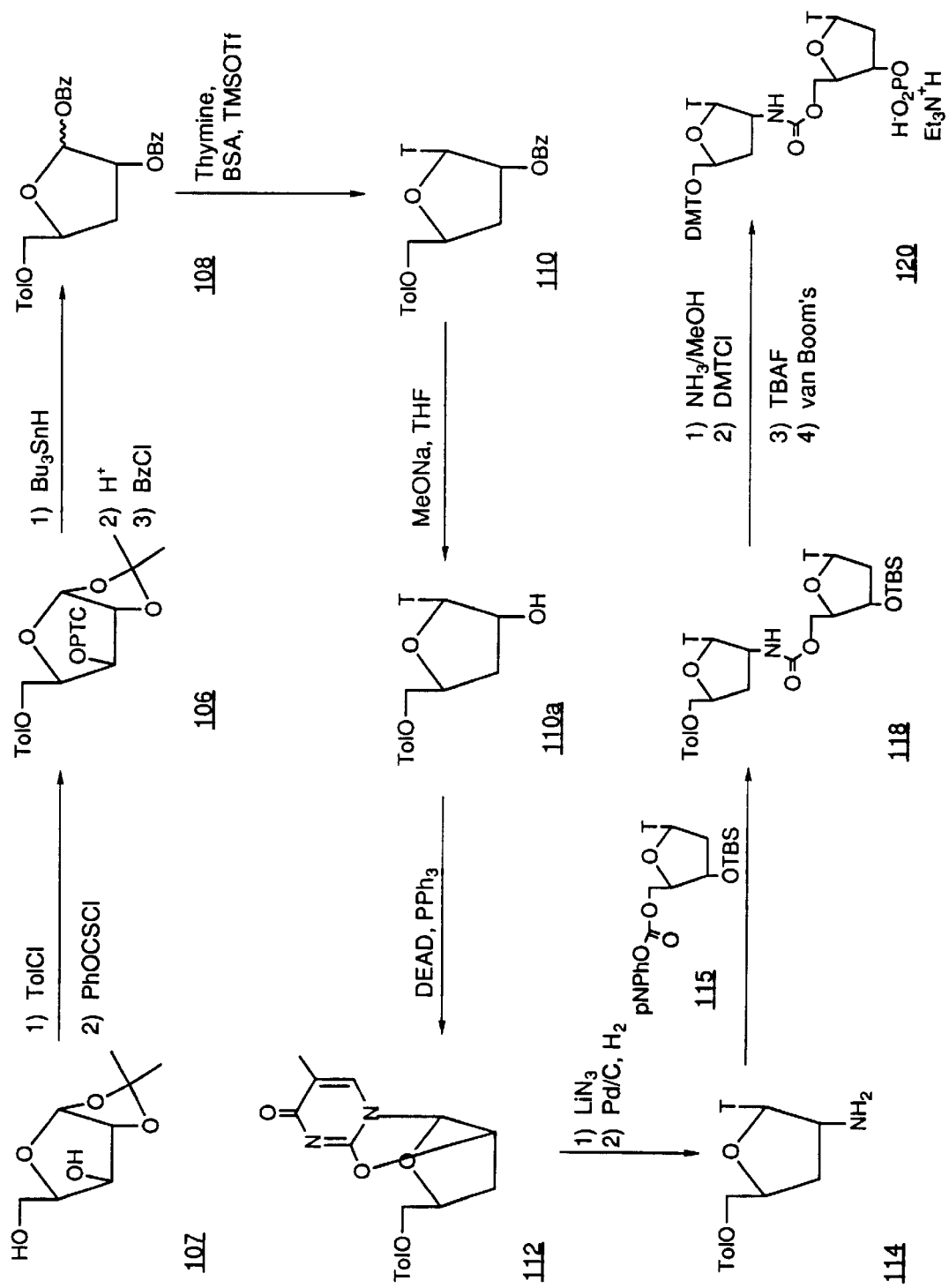
Figure 17:
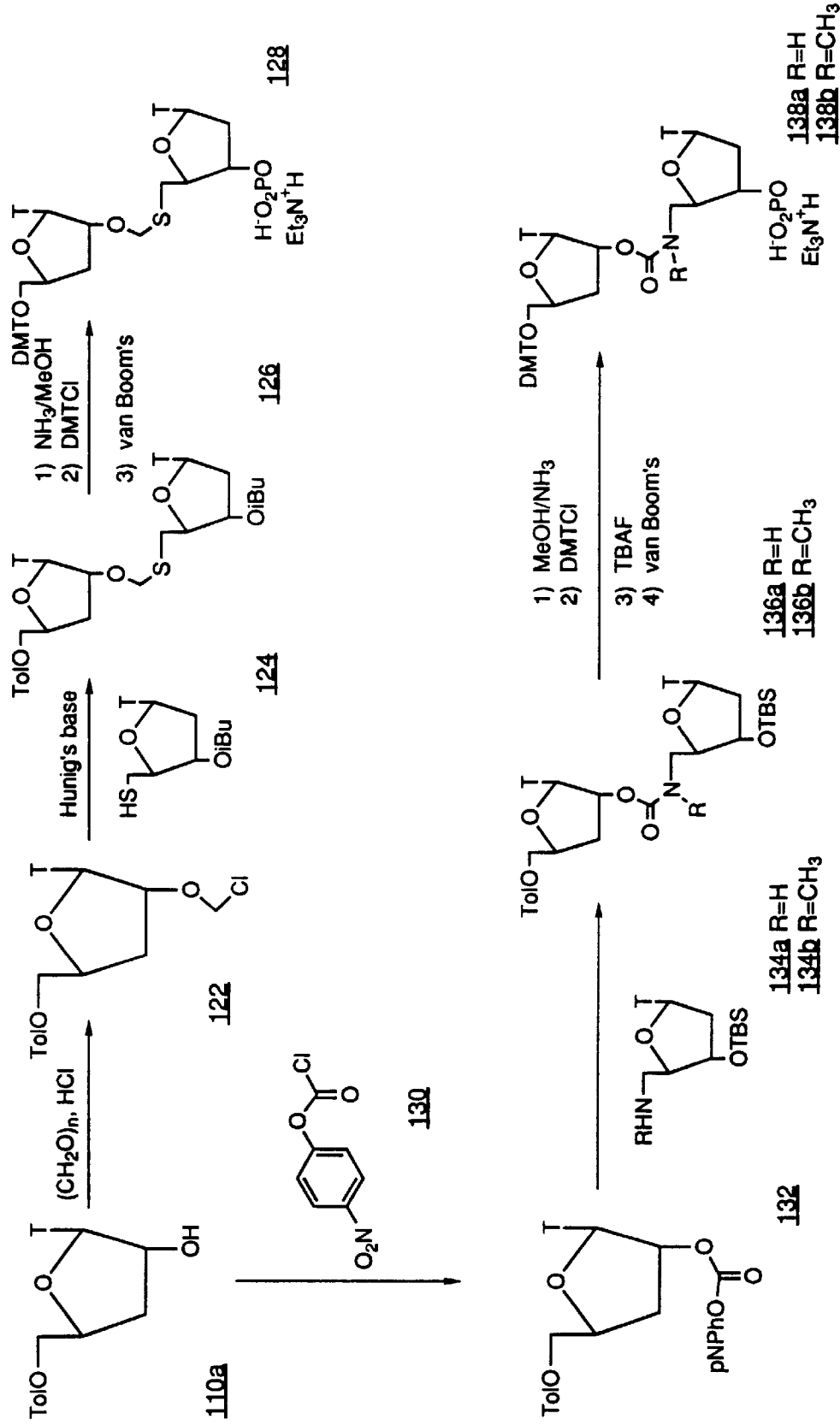

As can be seen from the variety of linkages specifically listed in Table 1, the linkages of the invention can vary so as to contain one or more nitrogen, sulfur, and/or oxygen atoms in their linking structure. The positions of these atoms in the linkage can vary from the "5'" end, to the "middle" to the "2'" end. In this section, a series of representative synthesis reaction schemes are set forth which provide routes to various locations and combinations of nitrogen, oxygen, and sulfur atoms within the linkages. Specifically, Scheme 1 shown in FIG. 1, shows the formation of a nucleotide dimer containing a three atom long linkage with a nitrogen at the 5' end of the 2' nucleoside. Scheme 2, depicted in FIG. 2, shows the formation of a three atom long linkage with a nitrogen at the 2' end of the 5' nucleoside. Scheme 3, shown in FIG. 3, depicts the formation of a three atom long linkage with a nitrogen in the middle. Scheme 4, shown in FIG. 4, depicts the formation of a four atom long linkage with oxygen at the 2' end and nitrogen at the 5' end. Scheme 5, depicted in FIG. 5, shows the formation of a four atom long linkage with nitrogen at the 2' end and oxygen at the 5' end. Scheme 6, shown in FIG. 6, depicts the formation of a two atom long linkage with nitrogen at the 5' end. Scheme 7, depicted in FIG. 7, shows the formation of a two atom long linkage with nitrogen at the 2' end. Scheme 8, represented in FIG. 8, shows the formation of three different three atom long linkages with sulfur at the 2' end. Scheme 9, represented in FIG. 9, depicts the formation of three different two atom long linkages with sulfur at the 2' end. Scheme 10, depicted in FIG. 10, shows the formation of three different two atom long linkages with sulfur at the 5' end. Scheme 11, shown in FIG. 11, depicts the formation of a two atom long linkage with oxygen at the 2' end. Scheme 12 as shown in FIG. 12 depicts the formation of a three atom long linkage with oxygen at the 5' end. Scheme 13, depicted in FIG. 13, shows the formation of several alkyl derivatives of a three atom long linkage with nitrogen at the 2' end. Scheme 14, shown in FIG. 14, shows the formation of a three atom long aminal derivative. Scheme 15, depicted in FIG. 15, demonstrates the preparation of a three atom long linkage with sulfur at the 2' end. Scheme 16, shown in FIG. 16, shows the preparation of a three atom long linkage with a nitrogen at the 2' end of the 5' nucleoside. Scheme 17, shown in FIG. 17, shows the preparation of two three atom long linkages having oxygen atoms at the 2' end of the linkage. These linkages have either an oxygen or a sulfur at the 5' end and a carbon or carbonyl midlinkage. These schemes can be modified as is known to those practicing in the area of oligonucleotide chemistry. For example, although protection of the bases is not always indicated in the synthesis schemes, such may be desireable and can be accomplished using reagents and techniques known in the art. See, e.g. *Protective Groups in Organic Synthesis* (Theodora W. Greene, John Wiley and Sons, 1981). Similarly, although the use of protective groups is shown in some cases, it is not always necessary to block the reactants in order to synthesize the exemplified modified oligomers.

Turning to FIG. 1, the first two steps shown in Scheme 1 relate to the derivatization of thymine to a protected nucleoside. The third and subsequent steps in Scheme 1 are directed to the synthesis of modified backbone materials. The starting materials such as the material shown as compound 1 in Scheme 1 are 2'-deoxy-2'-2-allyl nucleosides. These allyl materials are analogous to the 3'-deoxy-3'-2-propanyl thymidyl derivatives described in Flandor, J. and Yam, S. Y., supra.

In step 1 of Scheme 1, the reactive 5'-hydroxyl in the nucleoside sugar is reacted with dimethoxytritylchloride (DMTCl) to protect it and yields compound 2. Other equivalent protecting groups may be used. In the next step, the 2'-allyl group of Compound 2 is oxidized with $OsO_4/NaIO_4$ to yield the aldehyde intermediate 4. The aldehyde 4 is then reacted with a 5-deoxy-5'-amino-3'-protected nucleoside, which can be selected from a range of known compounds and the resulting imine is reduced. This reductive alkylation reaction can be advantageously carried out using a suitable catalyst such as titanium isopropoxide and cyanoborohydride (see Mattson, R. J. et al., supra). This yields a pair of protected nucleosides joined through a 2'—$CH_2$—$CH_2$—NH—5' modified internucleoside linkage. Compound 6 in Scheme 1 is representative.

Thereafter, the 3'-hydroxyl protecting group is removed to yield compound 7. The amine group in the internucleoside linkage is protected, such as with an FMOC group to yield compound 8 and a phosphonate group is added to the 3'-hydroxyl with Van Boom's reagent (VB) (Marugg, J. E. et al., *Tet Letters* (1986) 27:2661–2664). This yields dimer 9 which has two nucleosides joined through a —$CH_2$—$CH_2$—N(FMOC)— modified internucleoside linkage, a free 3'-phosphonate group and a blocked 5' position. This dimer can then be added into a growing oligonucleotide using conventional chemistry. Alternatively, the resulting dimer or oligomer may be succinylated as a convenient linker for coupling to a solid support, such as controlled pore glass (CPG). The coupled modified oligomer can be used as a starting material for standard oligonucleotide synthesis, as, for example, using H-phosphonate chemistry as described by Froehler, B., et al., *Nucleic Acids Res* (1986) 14:5399.

This synthesis involves deprotection of the 5'-hydroxyl using dichloroacetic acid in methylene chloride and treatment with a 5'-DMT-protected base 3'-phosphonate in the presence of acetyl chloride/pyrimidine/acetonitrile, and repetition of this deprotection and linkage protocol for any desired number of times.

Alternatively, the liberated 3'-OH can be linked via an ester linkage to a solid support analogous to standard oligonucleotide synthesis (Matteucci, M. et al., *J Am Chem Soc* (1981) 103:3185) for extension of oligonucleotide. The final product is removed from the solid support by standard procedures, such as treatment with iodine in a basic aqueous medium containing THF or other inert solvent, followed by treatment with ammonium hydroxide. Deprotection of the nucleotide bases attached to the added nucleotides is also conducted by standard procedures. Similarly, the FMOC group protecting the nitrogen present in the internucleoside linker can be removed conventionally and, if desired, replaced by other R groups as set forth herein.

The modified internucleoside linkage can be included at any arbitrary position in an oligonucleotide by substituting for a conventional monomer in the sequential synthesis, a protected dimer containing the modified linkage which has been synthesized, for example, by the steps set forth in Scheme 1 shown in FIG. 1.

Any DNA synthesis chemistry such as phosphoramidate or phosphonate chemistry can be used to link monomers or dimers in a manner analogous to that set forth above.

Turning to FIG. 2, a representative route (Scheme 2) is provided for generating a three atom long linkage with a nitrogen at the 2' position is shown. In Step 1 the $N_3$ group is reduced to an amine such as with hydrogen and a hydrogenitive catalyst to yield compound 12. Step 2 begins with an ester compound 13. This material is treated in Step 2 with base to hydrolyze the ester, and treated with acid to yield the free acid 14. The acid is then selectively reduced to the alcohol 15 using for example a borane reducing agent. The alcohol 15 is converted in Step 4 to the aldehyde 16 such as by using a carbodiimide and DMSO. Aldehyde 16 and amine 12 are then coupled in Step 5 and converted to phosphonate 18 in a manner analogous to that used in Scheme 1 by treatment with TBAF (Tetrabutyl ammonium fluoride), FMOC—NHS and Van Boom's reagent plus TEAB.

In Reaction Scheme 3 (shown in FIG. 3) the starting material is a 2'-alkyl substituted protected nucleoside such as 2. In Step 1 the alkyl double bond is isomerized by coupling the alkyl group to 19. Step 2 can be used to generate a 2'-aldehyde substituent present in compound 21. This aldehyde can then be coupled to the known amine 22 in Step 3 and converted to the phosphonate in Step 4 which are analogous to the steps described in Schemes 1 and 2.

In FIG. 4 a route for producing an oxygen- and nitrogen-containing linkage is given. A free 2' hydroxyl is reacted in Step 1 with allyl iodide in the presence of sodium hydride to couple the allyl group to the free hydroxyl and yield compound 26. The allyl group in 26 is then oxidized to an aldehyde 28 which is reacted with amine-substituted nucleoside derivative 5 in Step 3 to give the two nucleosides coupled through a linkage of the invention and yield "dimer 29" which is converted to the phosphonate form 30 using the methodology set out in Scheme 1.

Scheme 5, shown in FIG. 5, is essentially the "reverse" of Scheme 4 in that the nitrogen is placed in the 2' position and the oxygen in the 5' position. Essentially the same reactions are conducted using different blocking and substitution patterns to achieve the reverse orientation.

Scheme 6, shown in FIG. 6, provides a two atom long linkage. It employs as representative nucleoside analog starting materials, aldehyde 21 (produced in Scheme 3) and amine 5 (noted as available in Scheme 1). These materials are coupled and converted to a phosphonate in Steps 1 and 2 which are analogous to Steps 5 and 6 of Scheme 2.

Scheme 7 shown in FIG. 7 also involves a 2 atom linkage, this time with a nitrogen at the "5'" end. This reaction sequence starts with the known 5' nitrile 38 which is converted to an aldehyde 39 in Step 1. This aldehyde then is coupled to amine 12 (previously prepared) in Step 2 and converted to a phosphonate in Step 3, again analogous to Steps 5 and 6 of Scheme 2.

Scheme 8, shown in FIG. 8, provides a route to three atom long linkers containing materials having sulfur in various oxidation states at the 2' end of the linkage. The scheme begins with the known thiol 45. In Step 1 the alcohol group on compound 15 (produced in Scheme 2) is reacted with tosyl chloride. Tosylate 46 is then coupled with thiol 45 in Step 2 to yield sulfur-containing "dimer" 47. Dimer 47, having sulfur as —S— can be converted directly to a phosphonate as shown in Step 3. Alternatively the sulfur can be partially oxidized with $NaIO_4$ (Step 4) to

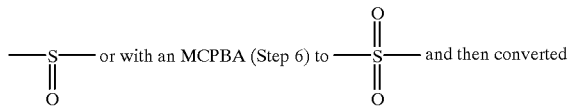

to the respective phosphonates as shown in Steps 5 and 7.

In Scheme 9 several two atom long sulfur-containing linkages are constructed. Aldehyde 39, prepared in Scheme 7 is reduced to alcohol 53 with a borohydride reducing agent. The alcohol is converted to a tosylate 54 which is then coupled to the thiol 45 from Scheme 8 in Step 3 to yield "dimer" 55. Dimer 55 is then converted to the phosphonate with or without oxidation in Steps 4, 5–6 and 7–8 respectively.

FIG. 10 shows Scheme 10 which is directly analogous to Schemes 8 and 9 just described with variation in the position of the aldehyde group and thiol group. Again, this scheme gives rise to 3 families of materials 67, 68 and 69 which differ from one another in terms of sulfur oxidation state.

Schemes 11 and 12 are representative routes to materials linked with oxygen present at the 2' and 5' ends of the linking group.

In Scheme 11, two routes are shown. In one a "5'" tosylate 46 is reacted with a "2'" alcohol 25 to yield dimer 71 which is converted to a phosphonate to yield 72. Alternatively a 2' tosylate 78 can be reacted with a 5' alcohol 77 to yield 71.

In Scheme 12, 2' aldehyde 4 is reduced to 2' alcohol 73 which is coupled to 5' mesylate 74 to give oxygen-containing linked material 75 which is converted to phosphonate 76.

FIG. 13, Scheme 13, shows the synthesis of alkyl derivatives of a 2' amine of a three atom long linkage. Azide 10 is hydrogenated to deliver the amine 12. Amines 81, 82 and 83 are treated with acetaldehyde toluene, and titanium isopropoxide and the products coupled with aldehyde 16, as described for amine 12, to yield dimers 84–86 which are in turn converted to the corresponding phosphonates 87–89. Acylated derivatives of the 2' amine begin with dimer 90, which is prepared as explained for compound 17. The products are ultimately converted to phosphonates as described further below.

The synthesis of an aminal-containing linkage (FIG. 14, Scheme 14) begins with amine 12, which is acylated to yield carbamate 99, which is alkylated to produce thioaminal 100 and is ultimately converted to the corresponding phosphonate.

Figure 15:
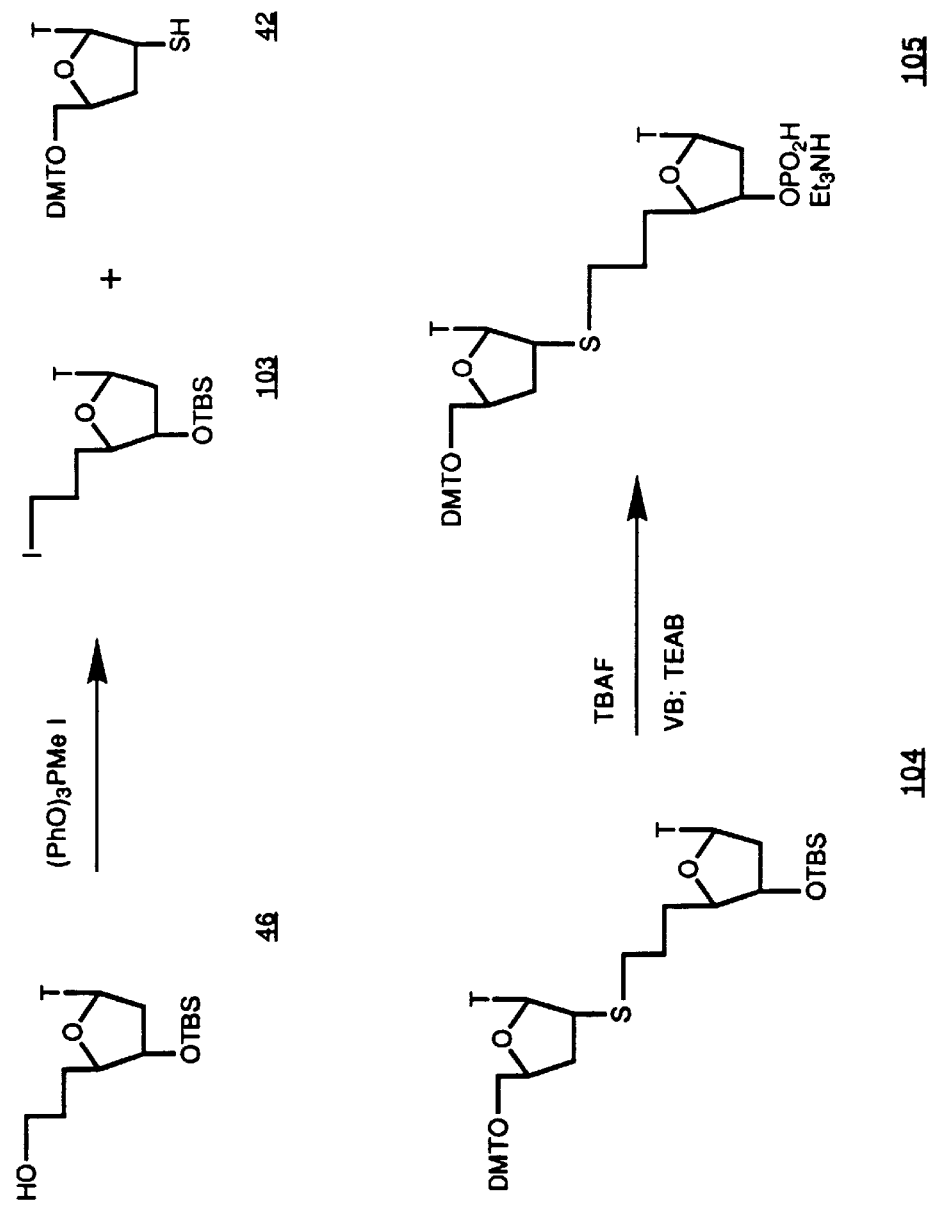

FIG. 15, Scheme 15, shows the preparation of a three atom long linkage with a 2' sulfur. Alcohol 46 (in DMF and pyridine) is reacted within methyltriphenoxyphosphonium iodide. The product is saturated with sodium thiosulfate to yield iodide 103. Thiol 42 and acetonitrile are combined with acetamide and DMF, and iodide added, to ultimately yield dimer 104 which is converted to a phosphonate 105 as described for compound 18.

The following examples are intended to illustrate but not to limit the invention.

D. Experimental

Example 1

The compounds of this example are shown in Scheme 1, shown in FIG. 1.

To a flask containing compound 1 (which may be produced using Scheme 18 as shown in FIG. 18) is added pyridine and the solution is evaporated to dryness. Pyridine is added again followed by DMT-Cl; the solution is stirred for 18 hours and poured in 10% aq sodium bicarbonate solution. The crude product is extracted with $CHCl_3$, dried ($Na_2SO_4$), stripped to dryness, and chromatographed on silica gel (5% MeOH/MC) (methylene chloride) to yield the product 2.

To a solution of 2 in dioxane and 1% aqueous sodium bicarbonate is added osmium tetroxide (2.5 wt % solution in t-butyl alcohol), and the solution stirred for 5 minutes. Sodium periodate is added in four portions, and the mixture stirred. The solution is poured into 10% aqueous saturated bicarbonate and the crude product is extracted with chloroform; dried ($Na_2SO_4$); and concentrated. The resulting oil is taken up in methylene chloride; filtered through celite and concentrated. To this aldehyde is added, 5'-amino, 3-(O-t dimethylsilyl)thymidine, toluene, and titanium tetraisopropoxide. After stirring for 1 hour, ethanol (20 ml abs) and sodium cyanoborohydride are added and the reaction stirred. The solution is poured into 10% aq sodium bicarbonate solution and the crude product extracted with chloroform; dried ($Na_2SO_4$); stripped to dryness, and chromatographed on silica (1% $Et_3N/5$ to 10% methanol/MC) to yield the product 6.

Compound 6 is dissolved in THF and tetrabutylammonium fluoride is added. The reaction solution is stirred, concentrated and applied to a silica gel column and chromatographed (1% $Et_3N/5$ to 10 to 15% MeOH/MC) to yield the product 7.

To a solution of compound 7 in acetonitrile and methanol is added N-(9-Fluorenylmethoxycarbonyloxy) succinimide, and the solution stirred. The crude product is concentrated to dryness; toluene is then added and the solution is again evaporated to dryness to deliver the product 8.

Compound 8 is dried by azeotropic distillation with pyridine. To a solution of 8 in pyridine and MC at 0° C. is added a solution of 2-chloro-4H-1,3,2-benzodioxaphosphorin-4-one (1 M in MC). The solution is stirred and quenched with pH 7.5 triethyl ammonium bicarbonate (TEAB). The crude product is extracted with 4:1 MC/n-butanol, dried ($Na_2SO_4$), and diluted with acetonitrile. The solution is concentrated and chromatographed on silica gel (1% pyr/O to 20% $H_2O$/acetonitrile). The product-containing fractions are concentrated, diluted with toluene and concentrated again. The product is then dissolved in 3:1 MC/n-butanol and back extracted with pH 7.5 triethylammonium bicarbonate. The organic layer is dried ($Na_2SO_4$), diluted with acetonitrile, and concentrated to afford the final product 9. The FMOC group can be substituted using conventional techniques.

Example 2

The compounds used and generated in this example are shown in Scheme 2, FIG. 2. A mixture of compound 10 obtained as shown in FIG. 19, Scheme 19, 10% palladium on carbon, ethyl acetate, and methanol is hydrogenated at atmospheric pressure. The reaction mixture is filtered through celite, and the solvent is evaporated. The crude product is chromatographed on silica gel (0.5% TEA/5% MeOH/MC) to yield the product 12.

Compound 13 is dissolved in dioxane and water and treated with lithium hydroxide. The solution is poured into ice cold 0.1M $H_3PO_4$ and chloroform. The crude product is extracted with chloroform, dried over $Na_2SO_4$, concentrated, and chromatographed on silica gel (5% methanol/MC) to yield the carboxylic acid 14.

To a solution of carboxylic acid 14 in tetrahydrofuran at 0° C. is added $BH_3$-THF (1.0M in THF) in three portions. The mixture is slowly poured into ice cold aqueous sodium bicarbonate. The product is extracted with chloroform, dried over sodium sulfate, and concentrated to provide alcohol 15.

A solution of 15 in DMSO is treated with N,N'dicyclohexyl carbodiimide (DCC) and dichloroacetic acid, and the mixture stirred. The reaction mixture is poured into 5% aqueous bicarbonate, and the crude product extracted with chloroform, dried over sodium sulfate, concentrated, and chromatographed on silica gel (5% MeOH/MC) to afford the aldehyde 16.

The aldehyde 16 and amine 12 may be coupled and then converted into the phosphonate 18 in analogous fashion as described for compound 6 (Example 1). Following synthesis, the FMOC group can be replaced using conventional methods.

Example 3

The compounds used and generated in this example are shown in Scheme 3, FIG. 3.

Preparation of 20: To a dry (azeotroped from pyridine at reduced pressure) sample of compound 2 is added dry $CHCl_3$ (ethanol-free) and stirred at room temperature until a solution results. To this solution is added 4-methyl-1,2,4-triazoline-3,5-dione. The resulting red solution should be protected from light and allowed to stir at room temperature overnight. More 4-methyl-1,2,4-triazoline-3,5-dione is added, and the reaction mixture is protected from the light and allowed to stir at room temperature overnight. The reaction mixture is diluted with $CHCl_3$ and the organic phase washed with saturated aqueous $NaHCO_3$, separated, and dried over $Na_2SO_4$. Removal of solvents affords a dark yellow oil, which is purified by column chromatography with Baker, Inc. silica gel, using a step gradient of 4%–20% isopropyl alcohol in $CH_2Cl_2$ as eluent. This will afford a clear oil, whose $^1H$ NMR spectral properties are consistent with the structure of 20.

Compound 20 is oxidized to 21. Compound 21 is coupled with amine 22 and may be subsequently converted into the phosphonate 24 in a similar manner to that described for compound 2.

The FMOC group may be substituted using conventional methods.

Example 4

The compounds used and generated in this example are shown in Scheme 4, FIG. 4.

To a solution of 25 in THF is added NaH (60% dispersion in oil), and the solution stirred. Allyl iodide is added, and the solution stirred for an additional period. The reaction mixture is poured in 5% aqueous bicarbonate, and the crude product is extracted with MC, washed with saturated brine, dried over sodium sulfate, and concentrated to deliver the product 26 as a crisp yellow foam.

Compound 26 is converted into aldehyde 28 in the manner previously described for compound 2. Aldehyde 28 is coupled with compound 5 and subsequently converted to the phosphonate 30 as described above.

The FMOC group may be substituted using conventional methods.

Example 5

Preparation of 5'-TCTCme($CH_2$—$CH_2$—NH)TCme($CH_2$—CH2—NH)TCme($CH_2$—$CH_2$—NH)TCme($CH_2$—$CH_2$—NH)TTTT-2'

The oligomer of this example is synthesized using the conventional techniques described by Froehler, B. C. et al., *Nucleic Acids Res* (1986) 14:5399, but with the incorporation of the Cme($CH_2$—$CH_2$—NFMOC)T dimer synthon. This dimer is constructed using the technique described in Example 1. The oligomers resulting from the synthesis may be deblocked with concentrated ammonia and gel purified using conventional techniques.

Example 6

Preparation of 5'—TCTCme(O—$CH_2$—$CH_2$—NH)TCme(O—$CH_2$—$CH_2$—NH)TCme(O—$CH_2$—$CH_2$—NH)TCme(O—$CH_2$—$CH_2$—NH)TTTT-2'

The oligomer of this example is synthesized as in Example 6, using the conventional techniques described by Froehler, B. C. et al., *Nucleic Acids Res* (1986) 14:5399, but with the incorporation of the Cme(O—$CH_2$—$CH_2$—NFMOC)T dimer synthon. This dimer is constructed using the technique described in Example 4. The oligomer resulting from the synthesis is deblocked with concentrated ammonia and gel purified using conventional techniques.

Example 7

Preparation of 5'-TCTCTC($CH_2$—$CH_2$—O)TC($CH_2$—$CH_2$—O)TCTTTT-2'

The oligomer prepared in this example consisted of conventional nucleotides as well as modified internucleoside linkages wherein the C preceding each of the modified linkers is a hydroxyethyl morpholino cytidine. This oligomer is synthesized as in Example 6, using the conventional techniques described by Froehler, B. C. et al., *Nucleic Acids*

Res (1986) 14:5399, but with the incorporation of the morpholine C(CH$_2$—CH$_2$—O)T dimer synthon. This dimer is constructed using the technique described in Example 5. The oligomers resulting from the synthesis may be deblocked with concentrated ammonia and gel purified using conventional techniques.

Example 8

Preparation of T (NR—CH$_2$—CH$_2$) T

The preparation of alkyl derivatives of the 2' amine, as shown in Scheme 13, FIG. 13 begins with azide 10. Compound 10 in methanol with 10% palladium on carbon is hydrogenated. The catalyst may be removed by filtration and the solvent removed by rotary evaporation to deliver the amine 12. To a solution of amine 12, acetaldehyde and toluene is added titanium isopropoxide and the solution stirred. At this point absolute ethanol (25 mmol) and sodium cyanoborohydride may be added. The mixture is subsequently stirred and stripped to dryness.

The crude product is chromatographed on silica gel (1% Et$_3$N/3 to 5 to 8% 2-propanol/MC) to deliver the product as a white foam. In a similar manner, amines 82 and 83 may be prepared. Compounds 81–83 are then coupled with aldehyde 16 as described for amine 12 to deliver dimers 84–86, which may then converted to the corresponding phosphonates 87–89 as described for compound 18.

The preparation of acylated derivatives of the 2' amine may begin with the dimer 90, which is prepared as described for compound 17. Dimer 90 is deprotected with tetrabutylammonium fluoride as described for compound 7 to yield dimer 91. To a solution of amine 91, ethyl acetate and 5% aqueous sodium bicarbonate is added ethyl chloroformate. The organic layer is separated, dried over sodium sulfate, and concentrated. The crude product is chromatographed on silica gel (3 to 5 to 10 to 15% 2-propanol/MC) to yield the product 92. Likewise, carbamate 93 is prepared. Compounds 92 and 93 are subsequently converted to the phosphonates 94 and 95 as described above.

Example 9

As is shown in Scheme 14, shown in FIG. 14, the aminal derivative 101 is prepared from amine 12, which is acylated with ethyl chloroformate to give carbamate 99. The carbamate 99 is alkylated with chloromethyl methylsulfide in the presence of sodium hydride to afford thioaminal 100. compound 100 is activated with bromine in the presence of alcohol 31 to deliver dimer 101, which is then converted to the corresponding phosphonate 102 using the method described above.

Example 10

The compounds of this example are shown in Scheme 15, FIG. 15. To a solution of alcohol 46 in DMF and pyridine is added methylthiophenoxyphosphonium iodide, and the reaction stirred. The reaction is quenched with methanol and the solvents removed on the rotary evaporator. The crude product is dissolved in methylene chloride; is extracted with aqueous saturated sodium thiosulfate and aqueous saturated sodium bicarbonate; dried; concentrated; and chromatographed on silica gel to deliver the iodide 103.

To a solution of thiol 42 (which may be produced using Scheme 18 in FIG. 18) and acetonitrile is added bis (trimethylsilyl) acetamide. The solvent may be evaporated; DMF and iodide 103 are added. The reaction is stirred and then quenched with aqueous saturated sodium bicarbonate. The crude product is extracted with methylene chloride; dried; concentrated; and chromatographed on silica gel to deliver dimer 104. Dimer 104 is converted to the phosphonate 105 as described above.

Example 11

Preparation of Compound 120

This Example shows the preparation of Compound 120. The synthesis is found in FIG. 16.

Compound 107 (Aldrich) was treated with toluyl chloride in pyridine/CH$_2$Cl$_2$ followed by an aqueous work-up. The resulting syrup was crystallized from ether/hexane to yield white needles (89%). This 5-toluyl compound was then treated with phenoxythionocarbonyl chloride and DMAP in acetonitrile followed by an aqueous work-up to yield a tan solid (106).

Compound 106 was treated with tributyltin hydride and AIBN in toluene at 80° C. for 4 hours. The solvent was removed in vacuo and the resulting oil subjected to column chromatography and eluted with 15% EtoAc/hexane to yield a clear, colorless syrup. This syrup was dissolved in dioxane/ 1N HCl and heated at 65° C. for 1 hour. The solvent was cooled and neutralized by addition of saturated aqueous NaHCO$_3$ (pH=6). The solution was then reduced in vacuo until a two phase solution was observed. The solution was diluted with EtOAc and washed with saturated aqueous NaHCO$_3$ and brine. The organic phase was decanted, dried, and reduced to a yellow syrup. This syrup was dissolved in pyridine/CH$_2$Cl$_2$ and treated with benzoyl chloride for 12 hours. The solvent was removed and the residue subjected to an aqueous work-up. The resulting syrup was subjected to column chromatography and eluted with 15% EtOAc/ hexane.

Thymine was silylated in acetonitrile with BSA at 70° C. and treated with a solution of compound 108 followed by TMSOTf. The solution was stirred for 1 hour, cooled, and subjected to an aqueous work-up. The resulting white foam was subjected to column chromatography and eluted with 55% EtOAc/hexane.

Compound 110 was dissolved in anhydrous THF and treated with MeONa followed by neutralization and an aqueous work-up. The resulting white foam was crystallized from Et2O to yield a white powder.

Compound 110a was dissolved in THF and treated with PPh$_3$ and DEAD at 0° C. for 30 minutes. The solvent was removed and the resultant oil subjected to column chromatography and eluted with 7% MeOH/CH$_2$Cl$_2$.

Compound 112 was dissolved in DMF and treated with LiN$_3$ and NH$_4$Cl at 100° C. for 8 hours. The solution was cooled and the solvent removed and the residue subjected to an aqueous work-up. The resultant foam was dissolved in EtOH and treated with 10% Pd/C. The suspension was then hydrogenated at 60 psi H$_2$ for 12 hours. The suspension was filtered and the filtrate reduced to a white foam.

Compound 114 was dissolved in DMF and compound 115 and TEA were added. This solution was stirred at room temperature for 90 minutes. The solvent was removed and the residue subjected to column chromatography and eluted with 4% MeOH/CH$_2$Cl$_2$.

Compound 118 was dissolved in MeOH/NH$_3$ and the sealed flask was heated at 70° C. for 12 hours. The solvent was removed and the residual foam was crystallized from Et$_2$O to yield a white powder. This powder was dissolved in pyridine and treated with DMTCl for 3 hours. The solvent was removed and the residue subjected to an aqueous work-up. The residual oil was subjected to column chromatography and eluted with 3% MeOH/$CH_2Cl_2$. The resultant white foam was dissolved in THF and treated with $Bu_4NF$ for 1 hour and the solvent was removed in vacuo. The resultant white foam was subjected to column chromatography and eluted with 8% MeOH/$CH_2Cl_2$ to yield a white powder. This powder was dissolved in pyridine/$CH_2Cl_2$ and cooled to 0° C. and treated with van Boom's reagent for 30 minutes. The solution was neutralized with TEAB (1N, pH=7) and extracted with $CH_2Cl_2$ and reduced to a white foam. This foam was subjected to column chromatography and eluted with 12% MeOH/$CH_2Cl_2$/0.5%TEA to recover compound 120.

Example 12

Preparation of Compounds 128, 138a, 138b

This Example, depicted in FIG. 17, shows two synthesis reactions for the preparation either of 5'-2' carbamate or 5'-2' methyl carbamate linkages.

Compound 110a (prepared using the procedure shown in FIG. 16) was dissolved in $CH_2Cl_2$ and cooled to 0° C. Paraformaldehyde was added and HCl (anhydrous) was passed through the suspension until a solution resulted. The flask was sealed and stored at 5° C. for 16 hours. After this time the solvent was removed to yield a white foam (compound 122) that was used without further purification in the following steps.

Compound 122 and compound 124 were dissolved in $CH_2Cl_2$ and Hunig's base was added. The resulting solution was stirred at room temperature for 3 hours. The solution was diluted with $CH_2Cl_2$ and subjected to an aqueous work-up. The resultant foam was subjected to column chromatography and eluted with 4%iPA/$CH_2Cl_2$ to yield a white foam containing compound 126.

Compound 126 was dissolved in MeOH and treated with MeONa (trace) at 50° C. for 1 hour. The solvent was removed and the solid subjected to column chromatography and eluted with 10%MeOH/$CH_2Cl_2$ to yield a white foam. This foam was dissolved in pyridine and treated with DMTCl and stirred at room temperature for 2 hours. The solvent was then removed and the residue treated to an aqueous work-up and the residual foam subjected to column chromatography and eluted with 6%MeOH/$CH_2Cl_2$ to yield a white foam. This foam was dissolved in pyridine/$CH_2Cl_2$ and cooled to 0° C. and treated with van Boom's reagent and stirred for 30 minutes. The solution was neutralized with TEAB (1N, pH=7) and extracted. The resulting white foam was subjected to column chromatography and eluted with 12% MeOH/0.5% TEA/$CH_2Cl_2$ to yield a white foam (compound 128).

In the other synthesis route depicted in FIG. 17, compound 110a was dissolved in pyridine and treated with p-nitrophenylchlorocarbonate and stirred at room temperature for 12 hours. The solvent was removed and the resulting foam subjected to column chromatography and eluted with 50%EtOAc/hexane to yield a white foam (compound 132).

Compound 132 was dissolved in DMF and treated with compound 134a and TEA. The solution was stirred at room temperature for 24 hours. The solvent was removed and the resulting yellow syrup subjected to column chromatography and eluted with 4%MeOH/$CH_2Cl_2$ to yield a white foam.

Compound 136b was prepared using the procedure described for compound 134a except that compound 134b was used as the reactant.

Compound 136a was dissolved in MeOH/$NH_3$ and heated in a sealed flask at 65° C. for 16 hours. The solvent was removed and the resulting white foam was crystallized from $Et_2O$ to yield a white powder. This powder was dissolved in pyridine and treated with DMTCl and stirred at room temperature for 3 hours. The solvent was removed and the residue treated to an aqueous work-up and subjected to column chromatography and eluted with 4%MeOH/$CH_2Cl_2$ to yield a white foam. This foam was dissolved in THF and treated with TBAF and stirred at room temperature for 45 minutes. The solution was diluted with EtOAc and subjected to an aqueous work-up. The resulting white foam was then crystallized from $Et_2O$ to yield a white powder. This powder was dissolved in pyridine/$CH_2Cl_2$ and cooled to 0° C. and treated with van Boom's reagent and stirred for 30 minutes. The solution was neutralized with TEAB (1N, pH=7) and extracted. The resulting white foam was subjected to column chromatography and eluted with 12%MeOH/0.5%TEA/$CH_2Cl_2$ to yield a white foam containing compound 138a.

Compound 136b was used in the same fashion as described just above in the preparation of compound 138a to yield compound 138b.

Example 13

RNA and DNA duplex and DNA-triplex experiments utilizing certain desirable modified internucleoside linkages of this invention were conducted to determine those linkages' effect on the Tm values of the resulting oligonucleotides.

These experiments were carried out in a buffered solution (140 mM KCl, 5 mM $Na_2HPO_4$, and 1 MM $MgCl_2$) at pH=6.6 (except for the 2'–5' carbamate which was buffered at pH=7.0) according to the following protocol: 0.15 ODs of the target RNA/DNA was combined with 0.1 OD of the oligomer being assayed in a sterile eppendorf tube and dried. To this mixture was added 300 λ of $T_m$ buffer and the solution was stirred. $T_m$ values were then determined by a first derivative plot of absorbance versus temperature. Thermal denaturation analysis was carried out with a heating rate of 0.25° C./min and absorbance was monitored at 260 nm.

The test oligomers that were synthesized for analysis were of the following sequence:

5'-TC'''TC'''TC'''TC'''TC'''T$^A$TT$^A$TT-3' where T=thymidine, $C^m$=5-methyl-2'-deoxycytidine, and $T^AT$=a thymidine-thymidine dimer with an experimental linkage of the structure detailed in the table below. All other linkages were phosphodiester.

Target Duplex Sequence (DNA)

```
5'AGAGAGAGAGAAAAA 3'   ← target strand

3'TCTCTCTCTCTTTTT 5'   ← complement of target

Single Stranded Target (DNA or RNA)
                                 ↓
5'TTTTTCTCTCTCTCT 3'        T =U for RNA
```

TABLE

| Compound | DNA-duplex | | DNA-RNA-duplex | | DNA-Triplex | |
|---|---|---|---|---|---|---|
| | $T_m$ | °C./subst | $T_m$ | °C./subst | $T_m$ | °C./subst |
| control | 49 | — | 62.5 | — | 29.8* | — |
| 2',5'-carbamate | 53.5 | +2.2 | 61.0 | −0.8 | 26.5* | −1.7 |
| control | 49 | — | 62.0 | — | 39.1 | — |
| 5'-2'carbamate | 53.0 | +2.0 | 60.5 | −0.8 | 45.1 | +3.0 |
| 5'-2'Me-carbamate | 53.0 | +2.0 | 61.0 | −0.5 | 45.3 | +3.1 |
| control | 49.5 | — | 61.5 | — | 39.1 | — |
| 5'-2' thioformacetal | 53.0 | +1.8 | 58.5 | −1.5 | 39.0 | 0 |

*pH 7.0

Thus, modified oligomers for use in oligonucleotide-based therapies have been disclosed. Although preferred embodiments of the subject invention have been described in some detail, it is understood that obvious variations can be made without departing from the spirit and the scope of the invention.

The results demonstrated that all linkages within the scope of the invention that were examined are binding competent. In some instances, notably in Hoogsteen binding to duplex DNA, binding is equal to or greater than corresponding control 3',5' phosphodiester linkages.

We claim as our invention:

1. An oligonucleotide comprising a two, three or four atom modified internucleoside linkage between the 2' and 5' position of adjacent nucleosides wherein the modified internucleoside linkage contains at least one carbon atom and at least one nitrogen, oxygen or sulfur atom, provided that no adjacent two or three atoms are all nitrogen, oxygen or sulfur, and wherein the oligonucleotide comprises a conjugate with a label, an intercalator, a drug or a lipophilic group.

2. The oligonucleotide of claim 1 wherein at least one modified internucleoside linkage is 2'-NH—C(O)—O-5', 2' O—C(O)—NH-5', 2'-O—C(O)—N(CH₃)-5' or 2'-O—CH₂—S-5'.

3. The oligonucleotide of claim 1 having the formula (W,Y)—Q—(Z—Q)ₙ—(W, Y) where each

Y =

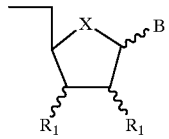

W =

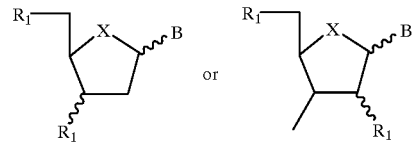

Z =

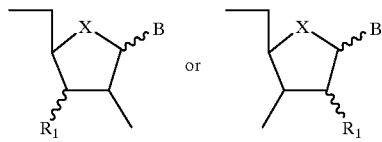

where X is S, O, CH₂, CHF or CF₂;

R¹ independently is —O-alkyl(C₁–C₁₂), —S-alkyl (C₁–C₁₂), H, OH, OCH₃, SCH₃, OC₃H₅, OC₃H₇, SC₃H₅, or F and where R¹ is on a terminal group of the oligomer, R¹ may additionally be PO₃⁻² or a blocking group selected from a dimethoxytrityl moiety, a monomethoxytrityl moiety, H-phosphonate, methylphosphonate or a phosphoramidite;

B is independently a purine or pyrimidine residue that binds to complementary nucleic acids by Watson-Crick pairing or by Hoogsteen pairing;

Q, is independently a phosphodiester linkage, a phosphodiester analog or a two, three or four atom modified internucleoside linkage between the 2' and 5' position of adjacent nucleosides; and n is 1–100, provided that at least one Q is a two, three or four atom modified internucleoside linkage between the 2' and 5' position of adjacent nucleosides.

4. The oligonucleotide of claim 3, wherein the oligonucleotide comprises a conjugate with a label.

5. The oligonucleotide of claim 1 which is a dimer, trimer or tetramer.

* * * * *